(12) United States Patent
Bartlett et al.

(10) Patent No.: US 11,659,990 B2
(45) Date of Patent: May 30, 2023

(54) SHAPE DISCRIMINATION VISION ASSESSMENT AND TRACKING SYSTEM

(71) Applicant: GENENTECH, INC., South San Francisco, CA (US)

(72) Inventors: Michael Bartlett, Richardson, TX (US); Yi-Zhong Wang, Richardson, TX (US)

(73) Assignee: GENENTECH, INC., South San Francisco, CA (US)

( * ) Notice: Subject to any disclaimer, the term of this patent is extended or adjusted under 35 U.S.C. 154(b) by 232 days.

(21) Appl. No.: 16/935,055

(22) Filed: Jul. 21, 2020

(65) Prior Publication Data

US 2020/0345227 A1 Nov. 5, 2020

Related U.S. Application Data

(63) Continuation of application No. 15/403,656, filed on Jan. 11, 2017, now Pat. No. 10,765,312, which is a
(Continued)

(51) Int. Cl.
*A61B 3/00* (2006.01)
*A61B 3/032* (2006.01)
(Continued)

(52) U.S. Cl.
CPC ............ *A61B 3/032* (2013.01); *A61B 3/0025* (2013.01); *A61B 3/0033* (2013.01);
(Continued)

(58) Field of Classification Search
CPC ..... A61B 3/0041; A61B 3/032; A61B 3/0033; A61B 3/0058; A61B 3/111; A61B 3/0091; A61B 3/028; A61B 3/02
See application file for complete search history.

(56) References Cited

U.S. PATENT DOCUMENTS 4,105,302 A * 8/1978 Tate, Jr. ................ A61B 3/028
351/210
4,403,840 A 9/1983 Okun
(Continued)

FOREIGN PATENT DOCUMENTS

CN 201929941 U 8/2011
JP H08140933 A 6/1996
(Continued)

OTHER PUBLICATIONS

SG Notice of Allowance and Supplementary Examination Report received for Patent Application No. 10201402138P, dated Sep. 17, 2020.
(Continued)

*Primary Examiner* — Mustak Choudhury
(74) *Attorney, Agent, or Firm* — Morrison & Foerster LLP

(57) ABSTRACT

A method to self-test vision of a user for use with a handheld vision tester includes receiving image data of the user's face, determining dimensions of the user's face based on the received image data, computing a user viewing distance based on the determined dimensions, displaying a vision test based on the computed user viewing distance, receiving user input responses to the vision test, and outputting results of the vision test from the user input responses.

20 Claims, 10 Drawing Sheets

Related U.S. Application Data continuation of application No. 14/849,682, filed on Sep. 10, 2015, now Pat. No. 9,743,828, which is a continuation of application No. 13/319,305, filed as application No. PCT/US2010/034084 on May 7, 2010, now Pat. No. 9,155,461.

(60) Provisional application No. 61/251,159, filed on Oct. 13, 2009, provisional application No. 61/176,885, filed on May 9, 2009.

(51) Int. Cl.
 A61B 3/11 (2006.01)
 A61B 3/12 (2006.01)

(52) U.S. Cl.
 CPC .......... *A61B 3/0041* (2013.01); *A61B 3/0058* (2013.01); *A61B 3/111* (2013.01); *A61B 3/1225* (2013.01)

(56) References Cited

U.S. PATENT DOCUMENTS

| | | | |
|---|---|---|---|
| 4,486,180 A | 12/1984 | Riley | |
| 4,511,228 A | 4/1985 | Von Gierke et al. | |
| 4,561,723 A | 12/1985 | Hamano et al. | |
| 4,750,830 A | 6/1988 | Lee | |
| 4,756,305 A | 7/1988 | Mateik et al. | |
| 4,863,258 A | 9/1989 | Greene | |
| 4,891,630 A | 1/1990 | Friedman et al. | |
| 4,971,434 A | 11/1990 | Ball | |
| 5,051,931 A | 9/1991 | Cheu et al. | |
| 5,088,810 A | 2/1992 | Galanter et al. | |
| 5,090,799 A | 2/1992 | Makino et al. | |
| 5,094,521 A * | 3/1992 | Jolson .................... | A61B 3/085 351/210 |
| 5,121,981 A * | 6/1992 | Waltuck ................ | A61B 3/0325 351/243 |
| 5,173,724 A | 12/1992 | Bonham et al. | |
| 5,436,681 A | 7/1995 | Michaels | |
| 5,515,069 A | 5/1996 | Dillon, III | |
| 5,539,481 A | 7/1996 | Vax | |
| 5,550,602 A | 8/1996 | Braeuning | |
| 5,568,209 A | 10/1996 | Priester et al. | |
| 5,589,897 A | 12/1996 | Sinclair et al. | |
| 5,596,379 A | 1/1997 | Kawesch | |
| 5,638,082 A | 6/1997 | Grimm | |
| 5,645,513 A | 7/1997 | Haydocy et al. | |
| 5,646,710 A | 7/1997 | Caskey | |
| 5,668,743 A * | 9/1997 | Kushelvesky .......... | A61B 3/032 73/620 |
| 5,737,060 A | 4/1998 | Kasha, Jr. | |
| 5,781,274 A | 7/1998 | Moreno | |
| 5,861,936 A | 1/1999 | Sorensen | |
| 5,864,384 A | 1/1999 | Mcclure et al. | |
| 5,883,692 A | 3/1999 | Agonis et al. | |
| 5,946,075 A | 8/1999 | Horn | |
| 5,956,128 A | 9/1999 | Itojima et al. | |
| 6,033,076 A | 3/2000 | Braeuning et al. | |
| 6,042,231 A | 3/2000 | Fateh | |
| 6,048,064 A | 4/2000 | Hosoi et al. | |
| 6,112,114 A | 8/2000 | Dreher | |
| 6,139,149 A | 10/2000 | Shafer et al. | |
| 6,227,668 B1 | 5/2001 | Mckinnon et al. | |
| 6,260,970 B1 | 7/2001 | Horn | |
| 6,293,675 B1 | 9/2001 | Eger | |
| 6,409,513 B1 | 6/2002 | Kawamura et al. | |
| 6,478,425 B2 | 11/2002 | Trajkovic et al. | |
| 6,494,579 B1 | 12/2002 | Weiss | |
| 6,533,417 B1 | 3/2003 | Sain | |
| 6,542,081 B2 | 4/2003 | Torch | |
| 6,568,809 B2 | 5/2003 | Trajkovic et al. | |
| 6,656,131 B2 | 12/2003 | Alster et al. | |
| 6,715,878 B1 | 4/2004 | Gobbi et al. | |
| 6,742,892 B2 | 6/2004 | Liberman | |
| 6,854,846 B2 | 2/2005 | Quigley | |
| 6,856,131 B2 | 2/2005 | Miyazawa et al. | |
| 6,997,556 B2 | 2/2006 | Pfleger | |
| 7,220,000 B2 | 5/2007 | Alster et al. | |
| 7,275,830 B2 | 10/2007 | Alster et al. | |
| 7,334,892 B2 | 2/2008 | Goodall et al. | |
| 7,350,921 B2 | 4/2008 | Ridings | |
| 7,367,675 B2 | 5/2008 | Maddalena et al. | |
| 7,448,753 B1 | 11/2008 | Chinnock | |
| 7,665,847 B2 | 2/2010 | Alster et al. | |
| 7,671,888 B2 | 3/2010 | Nogami et al. | |
| 7,789,510 B2 | 9/2010 | Fateh | |
| 7,891,812 B2 | 2/2011 | Larichev et al. | |
| 8,066,376 B2 | 11/2011 | Wang et al. | |
| 8,162,919 B2 | 4/2012 | Cull et al. | |
| 8,444,270 B2 | 5/2013 | Nordstrom | |
| 8,668,334 B2 | 3/2014 | Krenik | |
| 8,888,288 B2 | 11/2014 | Iravani et al. | |
| 9,033,508 B2 | 5/2015 | Bartlett et al. | |
| 9,039,182 B2 | 5/2015 | Huang | |
| 9,155,461 B2 * | 10/2015 | Bartlett ................ | A61B 3/0041 |
| 9,186,293 B2 | 11/2015 | Krenik | |
| 9,345,401 B2 | 5/2016 | Bartlett et al. | |
| 9,498,118 B2 | 11/2016 | Bartlett et al. | |
| 9,629,538 B2 | 4/2017 | Wang | |
| 9,743,828 B2 * | 8/2017 | Bartlett ................ | A61B 3/0033 |
| 10,179,081 B2 | 1/2019 | Krenik | |
| 10,765,312 B2 * | 9/2020 | Bartlett ................ | A61B 3/0041 |
| 2002/0113943 A1 | 8/2002 | Trajkovic et al. | |
| 2003/0016332 A1 | 1/2003 | Trajkovic et al. | |
| 2003/0157464 A1 | 8/2003 | Tanassi et al. | |
| 2003/0223038 A1 | 12/2003 | Alster et al. | |
| 2004/0036840 A1 | 2/2004 | Marino et al. | |
| 2004/0105073 A1 | 6/2004 | Maddalena et al. | |
| 2004/0141152 A1 | 7/2004 | Marino et al. | |
| 2005/0007550 A1 | 1/2005 | Turkov et al. | |
| 2005/0018132 A1 | 1/2005 | Fukuma et al. | |
| 2005/0124375 A1 * | 6/2005 | Nowosielski .......... | A61B 3/066 455/66.1 |
| 2005/0213033 A1 | 9/2005 | Sabel | |
| 2005/0264760 A1 | 12/2005 | Ikezawa | |
| 2006/0001831 A1 | 1/2006 | Sumiya | |
| 2006/0012674 A1 | 1/2006 | Kao | |
| 2006/0023163 A1 | 2/2006 | Foster | |
| 2006/0087618 A1 | 4/2006 | Smart et al. | |
| 2006/0092377 A1 | 5/2006 | Todd et al. | |
| 2006/0164597 A1 | 7/2006 | Hayakawa et al. | |
| 2007/0200927 A1 | 8/2007 | Krenik | |
| 2008/0137036 A1 | 6/2008 | Bedell et al. | |
| 2008/0204662 A1 | 8/2008 | Kanazawa et al. | |
| 2009/0060287 A1 | 3/2009 | Hyde et al. | |
| 2009/0192361 A1 | 7/2009 | Yoo et al. | |
| 2009/0257189 A1 | 10/2009 | Wang et al. | |
| 2009/0273758 A1 | 11/2009 | Wang et al. | |
| 2010/0012822 A1 | 1/2010 | Tafas | |
| 2011/0007267 A1 | 1/2011 | Erickson et al. | |
| 2011/0027766 A1 | 2/2011 | Yoo et al. | |
| 2012/0050685 A1 | 3/2012 | Bartlett et al. | |
| 2012/0050686 A1 | 3/2012 | Bartlett et al. | |
| 2012/0106813 A1 | 5/2012 | Drobe et al. | |
| 2012/0120051 A1 | 5/2012 | Liu et al. | |
| 2012/0249951 A1 | 10/2012 | Hirayama | |
| 2012/0250152 A1 | 10/2012 | Larson et al. | |
| 2014/0192316 A1 | 7/2014 | Krenik | |
| 2015/0216405 A1 | 8/2015 | Bartlett et al. | |
| 2015/0374226 A1 | 12/2015 | Bartlett et al. | |
| 2016/0045388 A1 | 2/2016 | Krenik | |
| 2016/0089017 A1 | 3/2016 | Wang | |
| 2017/0119245 A1 | 5/2017 | Bartlett et al. | |

FOREIGN PATENT DOCUMENTS

| | | |
|---|---|---|
| JP | H1057317 A | 3/1998 |
| JP | 2001145613 A | 5/2001 |
| JP | 2001161646 A | 6/2001 |
| JP | 2002209851 A | 7/2002 |
| JP | 2002315725 A | 10/2002 |
| JP | 2003290144 A | 10/2003 |
| JP | 2005313003 A | 11/2005 |

(56) References Cited

FOREIGN PATENT DOCUMENTS

| | | |
|---|---|---|
| JP | 2006126899 A | 5/2006 |
| JP | 2007286521 A | 11/2007 |
| JP | 2008055021 A | 3/2008 |
| KR | 20050089232 A | 9/2005 |
| WO | 199816150 A1 | 4/1998 |
| WO | 199952419 A1 | 10/1999 |
| WO | 200200105 A1 | 1/2002 |
| WO | 2002076301 A1 | 10/2002 |
| WO | 2003077511 A1 | 9/2003 |
| WO | 2004093668 A1 | 11/2004 |
| WO | 2007026368 A2 | 3/2007 |
| WO | 2007026368 A3 | 11/2007 |
| WO | 2008128192 A1 | 10/2008 |
| WO | 2008150476 A1 | 12/2008 |
| WO | 2008155544 A1 | 12/2008 |
| WO | 2009010291 A1 | 1/2009 |
| WO | 2010077563 A2 | 7/2010 |
| WO | 2010077563 A3 | 9/2010 |
| WO | 2010132304 A1 | 11/2010 |
| WO | 2010132305 A1 | 11/2010 |
| WO | 2011006095 A1 | 1/2011 |
| WO | 2014176070 A1 | 10/2014 |

OTHER PUBLICATIONS

Extended European Search Report dated Apr. 10, 2014, Applicant: Vital Art and Science Incorporated, European Patent Application No. 10775298.2, 9 pages.

Extended European Search Report dated Apr. 17, 2014, for European Patent Application No. 10775299, 10 pages.

Foreign Communication from A Related Counterpart Application, Chinese Application No. 201080026823.1, First Chinese Office Action dated Jan. 14, 2014, 10 pages with English Translation.

Foreign Communication from A Related Counterpart Application, Japanese Application No. 2012-510883, Japanese Office Action dated Jan. 7, 2014, 5 pages with English Translation.

Foreign Communication from A Related Counterpart Application, Japanese Application No. 2012-510884, Japanese Office Action dated Dec. 24, 2013, 2 pages.

Foreign Communication from a Related Counterpart Application, Russia Application No. 2011150045/14(075141); Decision on Grant of a Patent For Invention and Report on Examination Results dated Aug. 20, 2014; 6 pages with English Translation.

Hess, R.F. et al. (1999). "Are Judgements of Circularity Local or Global?," Vision Research 39:4354-4360.

ID Office Action received for Patent Application No. P00201405052, dated Aug. 9, 2019, (with English Translation), 4 pages.

ID Office Action received for Patent Application No. P00201405052, dated Jan. 10, 2020, (with English Translation), 4 pages.

IN Office Action received for Patent Application No. 8638/DELNP/2011, dated Nov. 12, 2018, (with English Translation), 6 pages.

International Preliminary Report on Patentability, dated Nov. 9, 2011, for PC Application No. PCT/US2010/034086, filed May 7, 2010, 6 pages.

International Preliminary Report on Patentability, dated Oct. 27, 2015, for PCT Application No. PCT/US2014/034105, filed Apr. 15, 2014, 10 pages.

International Search Report and Written Opinion, dated Jul. 28, 2014, for PCT Application No. PCT/US2014/034105, filed Apr. 15, 2014, 15 pages.

International Search Report and Written Opinion, dated Jun. 30, 2010, for PCT Application No. PCT/US2010/034084, filed May 7, 2010, 12 pages.

International Search Report and Written Opinion, dated Sep. 14, 2010, for PCT Application No. PCT/US2010/034086, filed May 7, 2010, 9 pages.

Jeffrey, B.G et al. (2002). "Circular Contour Frequency in Shape Discrimination," Vision Research 42:2773-2779.

Loffler, G. et al. (2003). "Local and Global Contributors to Shape Discrimination," Vision Research 43:519-530.

Translation of Korean application No. 10-2011-7029227 dated Aug. 1, 2014, Applicant: Vital Art and Science Incorporated, 5 pages.

U.S. Appl. No. 16/204,040, Krenik et al, filed Nov. 29, 2018. (Copy not submitted herewith pursuant to the waiver of 37 C.F.R. § 1.98(a)(2)(iii) issued by the Office on Sep. 21, 2004.).

U.S. Appl. No. 16/392,447, Wang et al., filed Apr. 23, 2019 (Copy not submitted herewith pursuant to the waiver of 37 C.F.R. § 1,98(a)(2)(iii) issued by the Office on Sep. 21, 2004.)

Wang, Y.-Z. et al. (2005). "Contributions of Local Orientation and Position Features to Shape Integration," Vision Research 45:1375-1383.

Wang, Y.-Z. et al., (Jun. 2002). "Shape Discrimination in Age-Related Macular Degeneration," Investigative Ophthalmology & Visual Science, 43(6):2055-2062.

Wang; Y.-Z. (Jun. 2001). "Effects of Aging on Shape Discrimination," Optometry Vision Science 78(6):447-454.

Wiemer, N.G.M et al. (2008, e-pub. Apr. 4, 2008). "Refractive Properties of the Healthy Human Eye During Acute Hyperglycemia," Graefs Archive for Clinical and Experimental Ophthalmology, 246(7): 993-998.

Wilkinson, F. et al. (1998). "Detection and Recognition of Radial Frequency Patterns," Vision Research 38:3555-3568.

\* cited by examiner

SHAPE DISCRIMINATION VISION ASSESSMENT AND TRACKING SYSTEM

CROSS-REFERENCE TO RELATED APPLICATION

This application is a continuation of U.S. application Ser. No. 13/319,305 filed on Nov. 7, 2011, entitled "Shape Discrimination Vision Assessment and Tracking System." U.S. application Ser. No. 13/319,305 is the National Stage of, and therefore claims the benefit of, International Application No. PCT/US2010/034084 filed on May 7, 2010, entitled "Shape Discrimination Vision Assessment System," which was published in English under International Publication Number WO 2010/132304 on Nov. 18, 2010, and has a priority date of May 9, 2009 based on provisional application No. 61/176,885 filed by Michael Bartlett, et al. and also has a priority date of Oct. 13, 2009 based on provisional application No. 61/251,159 filed by Michael Bartlett, et al. All of the above applications are commonly assigned with this National Stage application and are incorporated herein by reference in their entirety.

TECHNICAL FIELD OF THE INVENTION

This invention relates to techniques for the design and implementation of a vision testing and assessment system.

BACKGROUND OF THE INVENTION

Vision assessment today is most commonly carried out either with basic screening charts or by professional evaluation by a trained optometrist or ophthalmologist. Many well known screening tests are available. The well-known Snellen acuity chart is widely used, but other charts such as the "tumbling E" chart, the "Landolt C" chart, and the Amsler grid chart are also commonly used. Use of vision charts is suitable for analysis of common vision problems such as focusing disorders, but they are of limited value for monitoring more serious disorders such as diabetic retinopathy, age-related macular degeneration, and other serious disorders. These diseases have the potential to become active and degenerate rapidly. If not properly treated, permanent vision loss or even blindness may occur.

Of course, methods exist for diagnosing and treating these more serious conditions. However, they generally require expensive and sophisticated equipment that must be operated by a specially trained technician, such as an optometrist or an ophthalmologist. In fact, the only commonly available tool for self-monitoring of most retinal disorders is the paper Amsler grid test. The Amsler grid is simply a square grid ruled on paper or cardboard. The user tests each eye individually by fixating on the grid and noting any grid segments that appear to be missing, wavy, or distorted. While simple and low cost, the Amsler grid is difficult to use since the individual must subjectively assess their own condition, it is not quantitative, and it can be very hard for patients to determine if missing, wavy, or distorted grid segments are slightly more or less pronounced from one test to the next.

Hence, a low cost vision screening and assessment system that can detect the early signs of vision disorders, track their progress, and/or assess their relative severity is highly valuable. Such a system would allow persons to test their vision for serious vision disorders such as macular degeneration, diabetic retinopathy, glaucoma, and other disorders. Persons suffering from such disorders could use such a system to track their condition and validate the effects of their treatment in an objective and quantitative manner. And, of course, objective and quantitative vision testing can also be very useful to care providers in optimizing treatments for their patients.

SUMMARY OF THE INVENTION

To address the above-discussed deficiencies of the prior art, in one embodiment, there is provided a method to self-test vision of a user for use with a handheld vision tester. In this particular embodiment, the method comprises: allowing the user to trigger operations of the handheld tester; employing a touchscreen of the handheld vision tester to present different shapes, either statically or dynamically, generated by the tester to the user for vision self-testing; receiving user input responses to the different shapes via the touchscreen display; determining results of the vision self-testing from the user input responses; storing the results in the handheld vision tester; and transmitting the stored results to a healthcare provider. One of the different shapes may be a modulated version of another similar shape displayed at the same time. The modulated version of the another similar shape includes a modulated edge. The healthcare provider uses the results to enhance treatment routines.

In another embodiment, there is provided a handheld vision tester for vision self-testing by a user. The handheld vision tester comprises a touchscreen display, a control, and an interface port. The touchscreen display is configured to present different shapes, either statically or dynamically, to the user for the vision self-testing. One of the different shapes may be a modulated version of another similar shape displayed at the same time. The modulated version of the another similar shape includes a modulated edge. The control is configured to allow a user to trigger operations of the tester and allow the user to select, with the touchscreen display, one of the different shapes. The handheld vision tester is configured to determine results of the vision self-testing from the user selections and store the results in the handheld vision tester. The interface port is configured to transmit the stored results to a healthcare provider who uses the results to enhance treatment routines.

The foregoing has outlined various features of the invention so that those skilled in the pertinent art may better understand the detailed description of the invention that follows. Additional features of the invention will be described hereinafter that form the subject of the claims of the invention. Those skilled in the pertinent art should appreciate that they can readily use the disclosed conception and specific embodiment as a basis for designing or modifying other structures for carrying out the same purposes of the invention. Those skilled in the pertinent art should also realize that such equivalent constructions do not depart from the scope of the invention.

BRIEF DESCRIPTION OF THE DRAWINGS

For a more complete understanding of the invention, reference is now made to the following descriptions taken in conjunction with the accompanying drawings, in which.

DETAILED DESCRIPTION

Figure 1A:
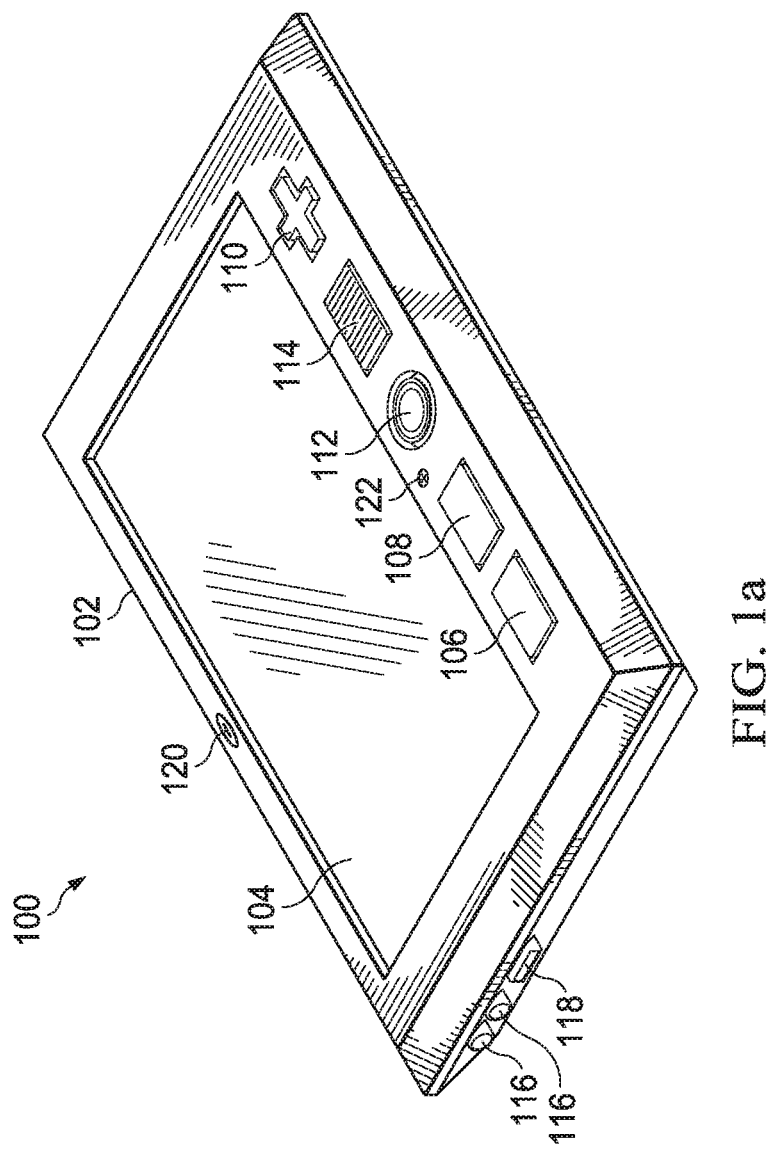
FIG. 1a shows a handheld device suitable for running a vision test.

In FIG. 1a, an electronic handheld device 100 is shown. The handheld device 100 may include a case 102, a display 104, a cursor control 110, a fingerprint sensor 114, a camera 112, a first button 106, a second button 108, a speaker 120, a microphone 122, a power connector 116, and an interface port 118. The display 104 may include touch-screen and/or multi-touch capability so that the handheld device 100 may be controlled by touching the display 104 in various locations or manners within certain timeframes. The fingerprint sensor 114 allows the handheld device 100 to identify the person using it (referred to as a user). Other techniques for positive identification such as voice analysis, passwords, biometric analysis, photographic analysis, and other possible techniques may also be implemented in the handheld device 100. It is also possible to positively identify the specific handheld device 100 that was used to take a specific test by recording an identifying number or code specific to that handheld device 100 with the records for that test. In addition, the identifying number or code for the specific handheld device 100 might be beneficially marked or engraved somewhere on or inside the case 102 or other location of the handheld device 100. Additional information regarding the user or the specific handheld device such as its date code, manufacturing date, serial number, and other information might also be beneficially marked, engraved, or otherwise indicated on or inside the handheld device 100. Warning messages, reminders, safety warnings and other information may also be marked on or inside the case 102. The cursor control 110 is a button that may be pressed to move a cursor across the display 104 and position it in a desired location. Pressing the cursor control 110 may also be used to trigger operations and to control the handheld device 100. Alternative implementations of cursor controls including track balls, joysticks, touch pads, and other approaches may also be used in place of the cursor control 110 as shown in FIG. 1a. The first button 106 and the second button 108 may be used to control the handheld device 100 and to operate functions of the handheld device 100. It is noted that the handheld device 100 may be operated through manipulation of the display 104 if a touch-screen or multi-touch capability is included, through the cursor control 110, through the fingerprint sensor 114, through the first button 106 and through the second button 108. Additional buttons and controls are possible including buttons and controls on the sides and back of the handheld device 100. It is also possible that the handheld device may include only one button, or no buttons at all. In addition, some embodiments of the handheld device 100 may include accelerometers, gyroscopes, or tilt sensors to monitor motion, rotation, and orientation of the handheld device 100 so that the handheld device 100 may be responsive to how it is held and physically oriented or moved. As a simple example, the use of a tilt sensor would allow the device to monitor and/or respond to it's orientation to preferentially use the display 104 in a portrait or landscape orientation. The handheld device 100 may also include a microphone 122 and audio processing capability to so that voice or sound commands may be used to control it. Also, the handheld device 100 may include a speaker 120, buzzer, vibrator, or other audible or physical signaling devices so that it can send messages and information to the user. Audible commands may benefit from use of a volume control that could be adjusted through the handheld device's 100 user control functions. And the camera 112 may be used to observe gestures, signals, sign language, and other symbols and movements of the user to control the handheld device 100 as well. Gestures involving actual motion of the handheld device 100 may be monitored with a motion sensor, accelerometer, or other techniques. It is also possible to include additional buttons, displays, an external mouse or trackball, and other forms of input devices. It is also noted that haptic, audible, or other feedback such as a click, buzz, vibration, jog, or other signal delivered on each button press, touch-screen or multi-touch press, or other activation of an input mechanism to the handheld device 100 may be beneficial to acknowledge the user's input and assure them that the handheld device 100 has or will respond to their inputs.

The case 102 of the handheld device 100 may be constructed from metals, plastics, or other materials. While not shown in FIG. 1a, the handheld device 100 may include removable panels on its front, back, or sides to allow batteries, memory cards, or optional accessories to be installed, connected, or removed. The power connector 116 allows the device to be powered from an external electrical power source that may supply AC or DC power to the handheld device 100. Some interface ports 118 (such UNIVERSAL SERIAL BUS (USB®)) may also be capable of supplying power to the handheld device 100. Interface port 118 allows the handheld device 100 to be connected to an external host computer, external cameras, external calibration or test equipment, external accessories, or other systems or devices the user may desire to connect it to. It is also possible that the interface port 118 or the power connector 116 could be configured to supply battery power from the handheld device 100 to an external device or interface connected to them. The interface port 118 may be constructed from multiple physical interfaces and protocols. Some examples are USB®, P1394, Ethernet, RS232, and many other possible interfaces. In addition to the interface port 118, the handheld device 100 may include wireless connectivity. BLUETOOTH®, IEEE802.11, ZIGBEE®, and many other wireless communications protocols and radio electronics may be included in the handheld device 100. The wired and or wireless connectivity of the handheld device 100 allows it to send information to a network service, host computer, or other computing device; and also allows for calibration, configuration, test protocols, software updates, and other useful information to be sent from a host computer or other data processing device or interface to the handheld device 100. The procedure for allowing the handheld device 100 to either send data out over its wired or wireless interfaces or to receive information from other sources should normally include security features to ensure that the user's information and privacy are not compromised and also to ensure that configuration, calibration, and other important factors of the handheld device 100 operation cannot be compromised illicitly or accidentally.

The handheld device 100 may be beneficially battery operated so that it can be used in a portable fashion in many locations when and where it is convenient for the user. Additionally, the handheld device may use power supplied to it over the interface port 118, the power connector 116, through wireless power sources, or through other possible ways of provide power to the handheld device 100. In the case of operation from an internal or external battery, the handheld device 100 may beneficially include capability to alert the user of the amount of charge available from the battery and alert the user when battery charging is needed. The handheld device 100 may also check the battery level before a vision test is begun to ensure that adequate energy is available to complete the test so that a test is not interrupted due to loss of power. The handheld device 100 may also include software routines constructed so that in the event of a sudden power loss the information stored in the handheld device 100 such as prior vision test results and other information is not corrupted or lost.

Figure 1B:
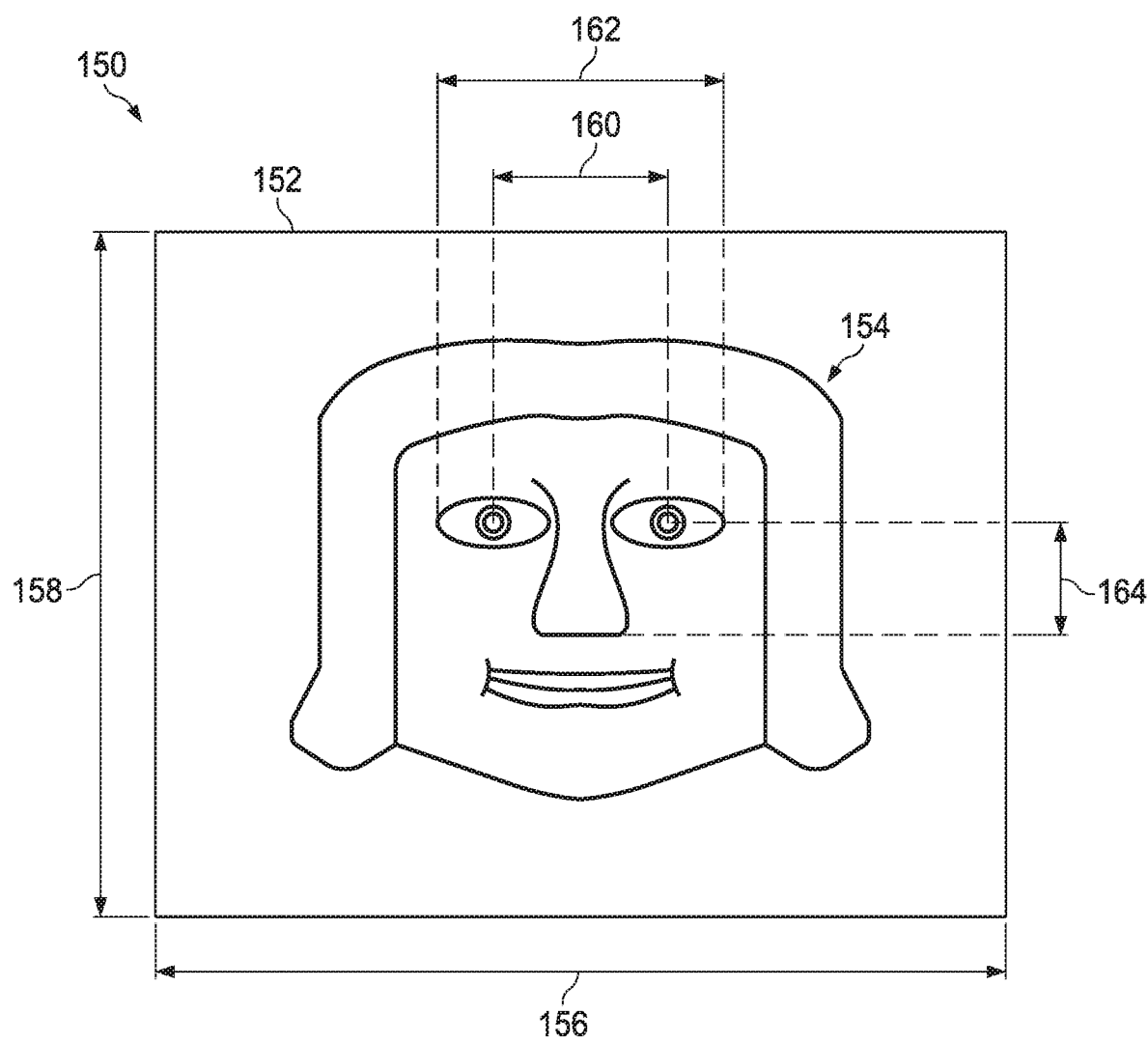
FIG. 1b shows an image of a user's face including key dimensions that may be used to determine the distance the user is away from the camera used to collect the image.

In this embodiment, the handheld device 100 is used to provide a vision test suitable for detected eye diseases and to monitor their present status or severity. As some vision tests are sensitive to the distance from the user under test to the display device being observed, it may be important that the handheld device 100 operate in a fashion that ensures that each test sequence is undertaken at an appropriate viewing distance. There are several options for how this can be achieved. First, the camera 112 may take a picture or even continuously monitor a video sequence of the user and make appropriate measurements from the image to ensure that the user is at an acceptable distance from the handheld device 100. An example of use of a camera image 150 to determine viewing distance is illustrated in FIG. 1*b*. In FIG. 1*b*, a camera image 150 of a user's face 154 is shown inside the camera's 112 image boundary 152. A horizontal image dimension 156 and vertical image dimension 158 are shown. Dimensions between some features of the user's face 154 are also shown. These are the distance between the pupils 160, the distance between the outer eye sockets 162 and the dimension between the pupils and the bottom of the nose 164. It is noted that for the purposes here of determining viewing distance that dimensions of the user's face 154 that are substantially unchanged by dress, mood, hairstyle, or other variable factors are preferred. That is, dimensions such as the distance between the pupils 160 are preferred over more variable dimensions such as the opening between the sides of the user's hair. Of course, many other dimensions of a user's face 154 may be used in addition to those shown specifically in FIG. 1*b*. By monitoring the distance between the pupils 160 or other dimensions of the user's face 154; and with the knowledge of the magnification afforded by the camera's 112 optics, it can be readily computed whether the user is a suitable distance from the handheld device 100. Such a technique for monitoring the distance the user is from the handheld device 100 may benefit from calibrating the actual dimensions of the user's face 154 to be used before testing begins. That is, if the handheld device 100 takes a photograph of the user when the user is at a known distance from the handheld device 100, then the handheld device 100 can compensate for the actual size of the facial features of a specific user and more accurately estimate the distance the user is subsequently from the handheld device than would otherwise be possible. Alternatively, the camera 112 optics could be calibrated against an object of known physical size, for example a ruler, placed at a know distance from the camera so that a reference image can be collected against which images may be compared. It is noted that the size of a dimension of the user's face 154 (or any other object for that matter) in a camera image 150 may not be a linear function of the distance it is from the camera 112. Consequently, use of non-linear correction factors or look-up tables may be beneficial in accurately computing the viewing distance from analysis of a given image 150. Of course, if the camera 112 includes a zoom capability or other variable optics, it may be beneficial to take distance measurements with the camera 112 set to a known and fixed level of zoom every time such measurements are taken. Alternatively, variations in zoom could be accounted for in the distance computation.

Of course, many other methods for measuring the distance from the handheld device 100 to the user are possible. Sonar, radar, light-based systems, and other electronic and photonic distance measurement devices can be incorporated into embodiments of the handheld device 100 to provide this function. Even simple mechanical techniques such as telescoping mechanical elements, strings that can be held from the user to the device, extendable chin rests, and many other techniques may be incorporated in to the handheld device 100 to ensure the user undertakes testing at an appropriate viewing distance.

If the handheld device 100 detects that the user is not at a suitable distance for the test that is operating, the handheld device 100 may signal to the user through a visible, audible, or other way that he or she is either too close or too far away. The handheld device 100 may not continue operation of the testing until the user has positioned himself or herself at an appropriate distance so that accurate and reliable testing is substantially ensured. If the camera 112 or some other means of monitoring the distance to the user from the handheld device 100 that can generate an image of the user is used; then it is further possible for the handheld device 100 to ensure that the test is being undertaken correctly. For example, in some vision tests, it is critical that the user cover one eye and undertake the testing one eye at a time. In such a case, the camera 112 can be used to monitor the user and ensure that the user has the correct eye covered for each test. The camera 112 can also ensure that the same person is taking the test throughout the test sequence and the image of the user can be compared to images from past tests to ensure that the person taking the test is indeed the correct person. Other information, such as ensuring that the user taking the test is awake and upright and is holding the handheld device at a proper orientation can also be checked.

It is noted that for some testing the handheld device 100 may automatically compensate for differences in desired viewing distances for some or all of the tests provided. That is, by monitoring how far the user is from the display 104, the handheld device 100 may compensate for some variations in the viewing distance by adjusting the size of the test image presented in the display 104 or by varying other aspects of the test image (for example, viewing distance may also be compensated to some degree with the sharpness of the test image or by other factors). By automatically compensating for changes in viewing distance, the handheld device 100 may make it easier for a user to take their test. Instead of compensating for viewing distance by altering the size or other features of the test image, the handheld device 100 may also account for alternative viewing distances by scaling the user's resultant test score appropriately. And, of course, combinations of ways to automatically compensate for differences in viewing distance may also be applied.

Visible glare that may appear on the display 104 of the handheld device 100 may be a substantial problem for accurate vision testing if it obscures test images and makes it difficult for the user to distinguish the images provided on the display 104. Use of a matte finished display (or other type of display that reduces glare) to reduce glare may be beneficial. In addition, the camera 112 may be used to sense ambient light conditions and alert the user to reduce ambient light or move to another location if too much ambient light is present that may result in glare or otherwise cause issues with vision testing. Scratches, smudges, chips, and other damage or contamination of the display 104 may also make accurate vision testing difficult. Use of a display 104 with a hard coating to avoid damage or with a screen protection film may be beneficial. As noted previously, a matte finish may be beneficial, so a matte finished screen protection film (or other glare reducing film) may be desirable. Additionally, the handheld device 100 may at times remind the user to clean and wipe off the display 104.

It is also possible to add auxiliary displays to the handheld device 100 or to use the interface 118 or wireless connectivity to move images and/or video to an external video monitor. Auxiliary displays suitable for use with the handheld device 100 include LCD display panels, CRT displays, light processing display devices, head mounted displays, binocular display devices, virtual reality viewers, and many other types of displays. One example is use of the very small projectors that are now available and can be incorporated into small devices and allow images and video to be expanded for easy viewing. These small projectors are sometimes referred to as pico-projectors. Such a pico-projector may be physically integrated into the handheld device 100 or may be used as an external separate device connected to the handheld device 100 through a wired or wireless communication link.

If an auxiliary display is used, the handheld device 100 may include hardware and software to ensure that proper viewing distance and display properties are available so that a reliable test may be completed. Hence, while images used for regular purposes may be displayed on a wide variety of available displays, the handheld device 100 might only send images or video for vision testing to displays that it can ensure are suitable for good quality testing. This requirement may impose the need for additional connectivity to an auxiliary display and also additional calibration and security features if the auxiliary display is to be used for vision testing.

The functions of the handheld device 100 shown in FIG. 1a may also be incorporated into electronic handheld devices that are already used for other functions. That is, the function delivered by the handheld device 100 may be implemented on a portable game console, a cellular phone, a personal digital assistant, a tablet computer, a netbook computer, a notebook computer, a blood glucose meter, or many other electronic devices. It is noted that there may be some benefit to using devices with somewhat larger displays as a greater area of the retina can be covered in vision testing (this may be more important for some vision disorders, but will be less important for others). However, larger devices with larger displays are normally less portable and may be more expensive, so tradeoffs of cost and convenience versus retina test coverage may need to be made. The ability to combine many functions together into a single device allows for convenience for the user and also allows for beneficial combined functionality in some cases. For example, if the handheld device 100 of FIG. 1a includes the function of a glucometer, the user can record their blood glucose level when each vision test is taken so that a more complete record of vision capability and blood glucose can be generated (and this may be especially beneficial to users at risk with regard to diabetic retinopathy). If the handheld device includes a positioning technology such as the Global Positioning System (GPS), the records of vision testing can be location stamped so that the user can more easily remember where they took each test and what the testing conditions were. Of course, the handheld device 100 can easily include calendar and clock functions so that test results may also be time and date stamped.

Figure 2A:
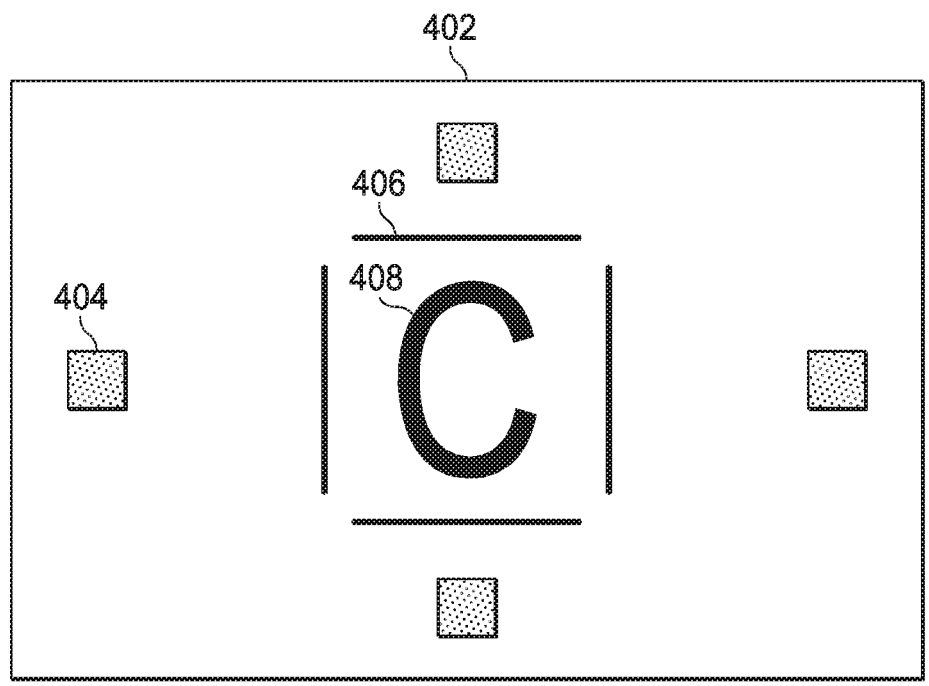
FIG. 2a shows a Landolt C image for vision testing.

In FIG. 2a, a Landolt C 408 test image is shown. The Landolt C 408 test is suitable for use with the handheld device 100 already described. The test image includes a display 104 outer boundary 402, soft keys 404, and reference lines 406. In this test, the Landolt C 408 is rotated in 90 degree increments so that the "open" side of the "C" points to the right (as shown in FIG. 2a), to the left, upwards, or downwards. The user performs the test by pressing the soft key 404 in the direction in which the Landolt C 408 has its opening. The Landolt C 408 test provides for a vision acuity check. The test can be easily extended to include additional angles of orientation for the directions in which the "open" side of the "C" can appear in the course of a test. As noted previously, it is important that the Landolt C 408 test be conducted at an appropriate viewing distance. The display 104 outer boundary 402 is the limit of the display 104 area used for the test. It is noted that depending on the actual design of the handheld device 100, the outer boundary 402 may be less than the physical limit of the display 104. For example, to test for a high level of vision acuity, the Landolt C 408 may appear rather small in the handheld device 100 display 104, so the entire display 104 area may not be used for some tests. The reference lines 406 are optional for the Landolt C 408 test and are included to better define the region in which the Landolt C 408 is rotated. Also, it is noted that the soft keys 404 may be pressed manually by the user with their fingers or with a stylus if that is preferred. And, instead of using the soft keys 404 for the user to provide their input on the orientation of the Landolt C 408, this may be indicated by touching the touch-screen at a pre-defined location (perhaps in the "opening" of the C), by strokes on the touch-screen, by gestures monitored by the camera 112, by movements of the handheld device 100, through voice signals, or by other techniques.

The Landolt C 408 test is based on a user's ability to distinguish the orientation of the "C" as a function of how large the image is presented. Of course, many other shapes may be used to create similar tests. Another common similar test is known as the "tumbling E" test. The "tumbling E" test is very similar to the Landolt C 408 test, the only key difference being the use of a letter E instead of a letter C. Of course, a very wide variety of shapes, such as circles, squares, triangles, and many other shapes that include some distortion, modulation, or other feature that allows their orientation to be specific so that a user can be challenged to identify it.

Figure 2B:
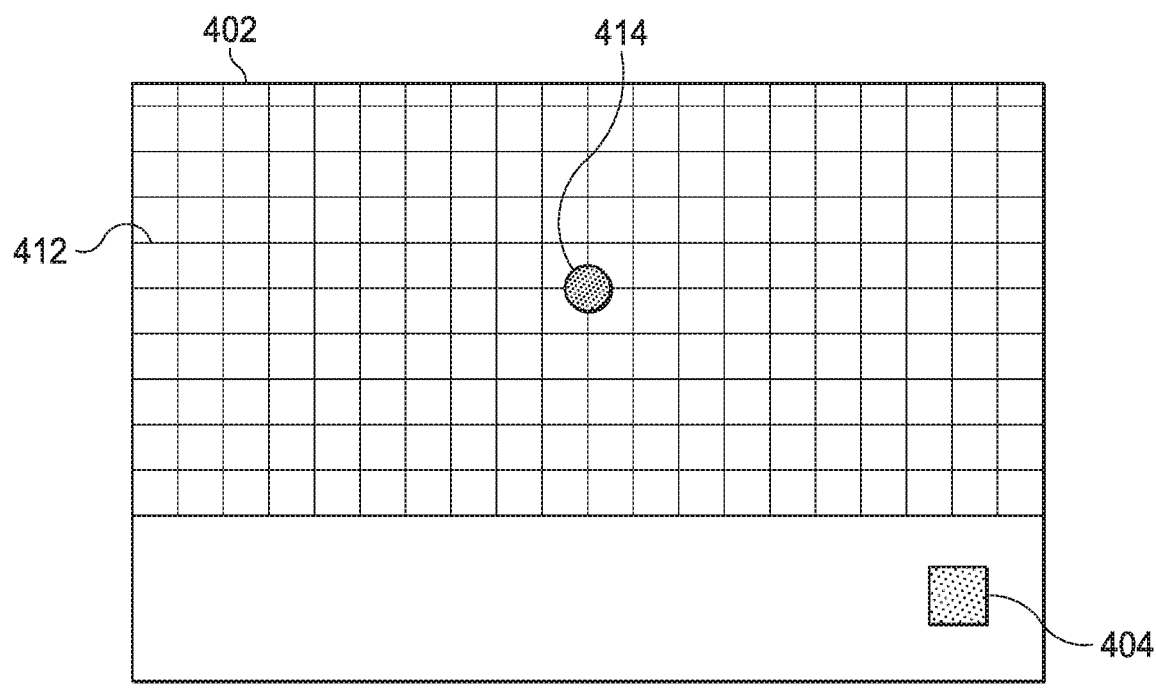
FIG. 2b shows an Amsler grid image for vision testing.

In FIG. 2*b* an Amsler Grid test image is shown. The Amsler Grid consists of grid segments 412 arranged in a regular rectangular grid within the outer boundary 402. A center feature 414 is provided for the user under test to fixate on while identifying any missing, wavy, or distorted grid segments 412. With a touch-screen capability in the display 104, it is very easy for the user to indicate which grid segments 412 are missing, wavy, or distorted simply by pressing on the display 104 above such a grid segment 412. With multi-touch capability in the display 104, the user may be able to indicate the location of missing, wavy, or distorted grid segments even more quickly and conveniently. It is possible to separately track which grid segments 412 appear to be missing, wavy, or distorted and this information is useful in keeping track of the status of an eye disease over subsequent tests. That is, a missing grid segment 412, may signal a more severe or advanced condition than a wavy or distorted grid segment 412, so information for each level of condition can be collected separately and tracked automatically. The soft key 404 shown in FIG. 2*b* can be used to indicate that the user sees all grid segments 412 normally. It is also noted, that the Amsler Grid test, like all tests described here, can be performed with different light intensities, colors, feature sizes, line weights, contrasts, and other image parameters to test the sensitivity and capability of the user's vision in a wide array of conditions.

Figure 2C:
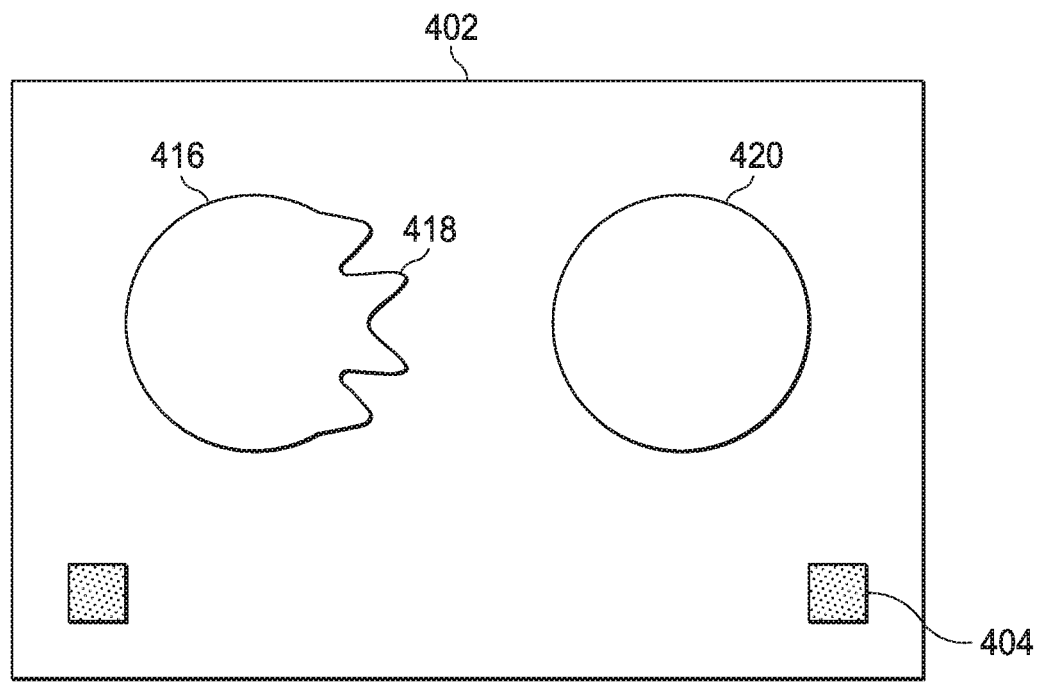
FIG. 2c shows an image for vision testing, including a reference circle and a circle with a modulated region.

FIG. 2*c* shows an image for vision testing that includes a right circle 420 and a left circle 416 either of which may include a modulated region 418. The outer boundary 402 serves the same function as in the prior figures. The soft key 404 is pressed by the user under test to indicate which of the two circles, the right circle 420 or the left circle 416 has a modulated region 418. Of course, this selection can be done directly by touching the circle that has a modulated region 418 if a touch-screen display is used. And other methods of capturing this input from the user based on visible gestures, movement of the handheld device 100, sounds, etc. are also possible. By changing the amplitude and location of the modulated region 418 and whether it appears on the left circle 416 or the right circle 420 it is possible to determine the user's ability to differentiate the presence or absence of a modulated region 418. Of course, other shapes besides circles such as hexagons, squares, and other shapes can be used. And the modulated region 418 need not be a smooth curve as shown in FIG. 2*c*, but may be triangular, rectangular, or of other shapes. The modulated region 418 may also appear at any angle around the circle including the top, the bottom, either side, or at other angles. And, of course, different colors, line weights, contrasts, brightness levels, and other factors may be varied so that the user under test's ability to distinguish the modulated region 418 under varying conditions can be determined. Depending on the display 104 size and format, the circles may be placed in any location on the display and not to the right and left as shown in FIG. 2*c*. And additionally, while FIG. 2*c* shows two circles, it is possible to create a similar test using three, four, or any number of circles or other shapes. With a larger number of circles or other shapes used in vision testing, the user selects from a broader number of choices and this may create a test with desirable attributes (the test may run faster, have more redundancy, be more accurate, or have other desirable attributes). It is also possible to use a single shape, such as the modulated left circle 416 shown in FIG. 2*c* with modulated region 418 in the manner of the Landolt C 408 test already described. In such a test, the orientation of the modulated region 418 is changed along with the amplitude of the modulation 418 and/or the size of the left circle 416 as the user's ability to properly distinguish the orientation is monitored.

In addition to the static images shown in the vision test in FIGS. 2*a*-2*c*, it is also possible to use dynamic images for vision testing on the handheld device 100. Images that open or close (expand or contract), or move in other ways can be observed and/or compared to other dynamic or static images to help test for vision capability.

Figure 3A:
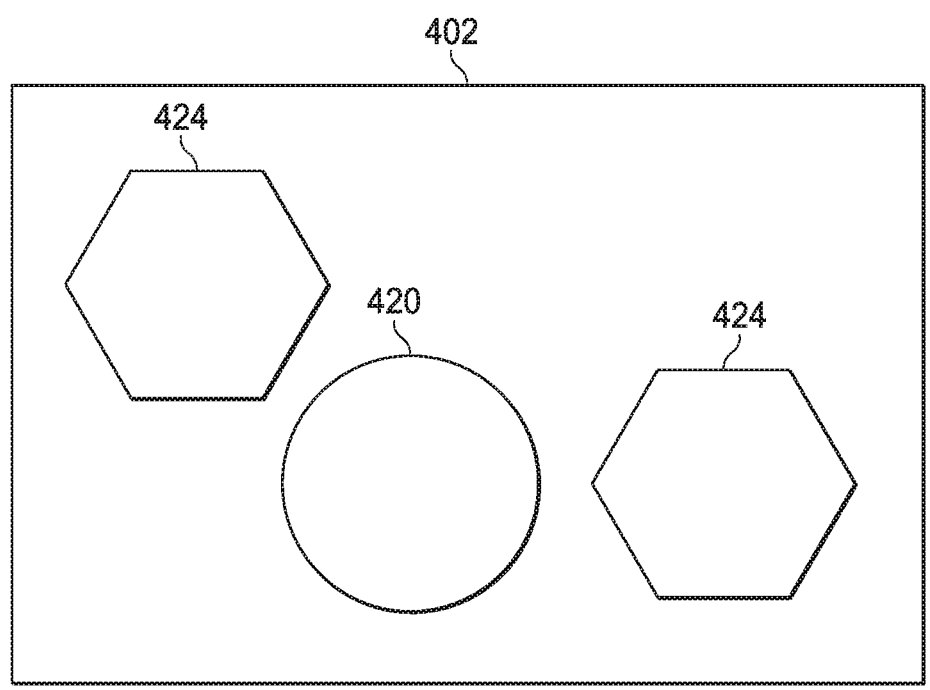
FIG. 3a shows an image for vision testing made up of multiple shapes in which one shape, a circle, is different from the other two, which are hexagons.

FIG. 3*a* shows an image for vision testing suitable for use on a handheld device 100 made up of multiple shapes in which one shape, a circle 420, is different from the other two, which are hexagons 424. The display boundary 402 is shown for reference. In this vision test, the user selects the shape that is different from the other two by touching it on a touch-screen display 104. Of course, this input could also be done with a keyboard, mouse, cursor controller 110, soft keys, audible signals, gestures, movement of the handheld device 100, or by other techniques. It is notable that in the image of FIG. 3*a*, there is no point of fixation at which the user must concentrate their vision. In fact, the purpose of such a test is to force the user to employ their broader vision capability in identifying which of the three or more shapes is different from the others.

Once the user selects which of the shapes in the image shown in FIG. 3*a* is different from the others, in the embodiment as shown it is clearly the circle 420, a subsequent test image may be presented to the user. This subsequent test image may be similar to the embodiment shown in FIG. 3*b*. Note that FIG. 3*b*, like FIG. 3*a*, includes a display boundary 402, a circle 420 and two hexagons 424. However, the locations of the circle 420 and hexagons 424 have shifted inside the display boundary 402. This is done intentionally to avoid the user fixating on one location in the test image and to encourage use of the user's broader vision. As with FIG. 3*a*, the user when viewing FIG. 3*b* would once again correctly select the circle 420 as the shape that is different from the other two.

Figure 3B:
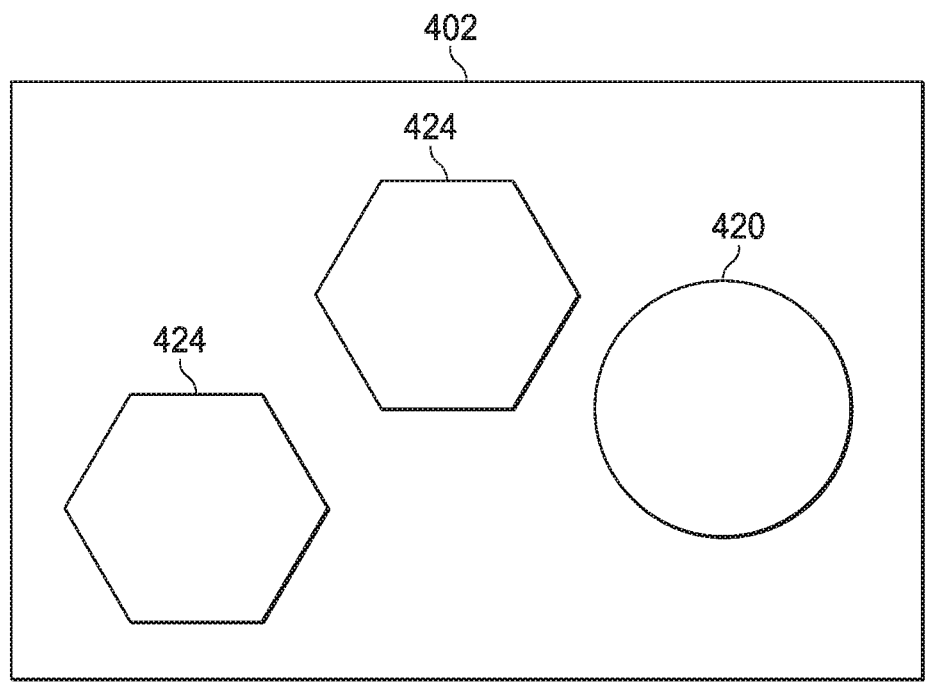
FIG. 3b shows an image similar to the one of FIG. 3a, but where the shapes have been moved to other locations on the screen to avoid creating a point of fixation.

While FIGS. 3*a* and 3*b* used circles 420 and hexagons 424 for shapes to be compared, may different shapes may be used. Squares, triangles, octagons, rectangles, and many other shapes can be applied. And while the circles 420 and hexagons 424 were relatively easy to distinguish from each other, shapes may be used that have only subtle differences so that the user is challenged to discriminate between them. In a vision test, a variety of easier and more difficult challenges in shape discrimination may be presented to the user so that the user's capability to detect small differences in shapes can be assessed. The subsequent images used for such testing may progressively become more difficult to distinguish as testing progresses, they may become more difficult based on some rules regarding the ability of the user to discriminate shapes in prior images, or may even be presented to the user randomly. Very many sequences for presenting more or less difficult shapes to discriminate are possible. It is also possible to make use of shapes that are turning, moving, changing size, rotating, or otherwise being altered in time as the test is taken.

Figure 4A:
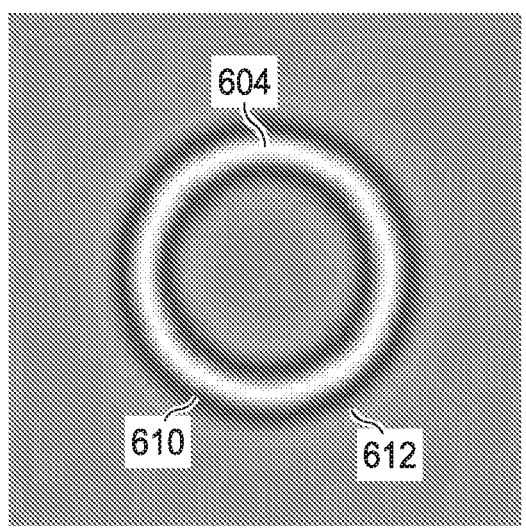
FIG. 4a shows a circle with pre-defined contrast as a function of radial dimension.

In FIG. 4*a*, a circle 604 is shown that has pre-defined contrast as a function of radial dimension. The circle 604 is shown as a light circular region on a gray background. It also includes dark halos 610 and light halos 612 on both the inside and outside of the light circular region. It is noted that the contrast level of the dark halos 610 and the light halos 612 are a function of the radial dimension of the point of consideration on the halo to the center of the circle 604. The use of a circle 604 that has pre-defined contrast as a function of radial dimension is beneficial in further encouraging the user of a vision testing system to avoid a specific point of fixation and instead employing their broader vision capability. Use of shapes with pre-defined contrast as a function of radial dimension also relaxes the dependence of test results on viewing distance. Hence, if shapes including pre-defined contrast such as the circle 604 of FIG. 4a were used in the test described in FIGS. 3a and 3b, some benefit in the accuracy of the testing may be achieved. Of course, many shapes including pre-defined contrast may be used instead of circles. Squares, triangles, ovals, ellipses, and many other shapes may be used. Also, the shapes need not be regular (that is, irregular shapes may also be used) and it is not even needed that they be closed curves. And, in addition to varying contrast with radial dimension, other aspects of the shape such as how sharp or fuzzy the lines are, brightness, color, and any other aspect of how the shape is presented may be varied.

Figure 4B:
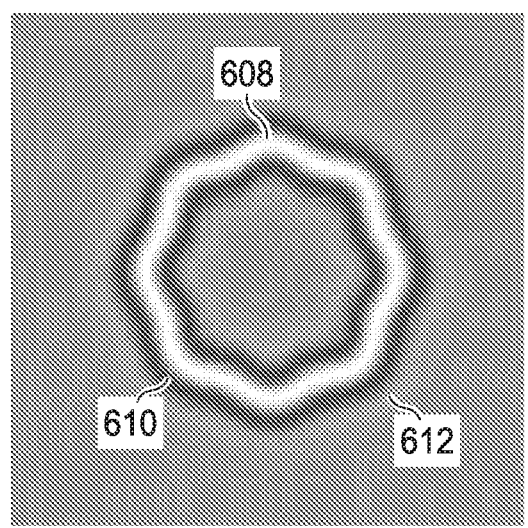
FIG. 4b shows a modulated circle with pre-defined contrast as a function of radial dimension.

In FIG. 4b, a modulated circle 608 is shown that has pre-defined contrast as a function of radial dimension. The modulated circle 608 is shown as a light region on a gray background. It includes dark halos 610 and light halos 612 on both the inside and outside the light region. The modulated circle 608 of FIG. 4b is very similar to the circle 604 of FIG. 4a with the exception that it has a modulated radius and is not a regular circle. Note that when the modulated circle 608 was formed, the pre-defined contrast as a function of radial dimension was applied first and the circular shape was then modulated so that both the light region and the dark halos 610 and light halos 612 were all modulated all together. The modulation applied in FIG. 4b is a smooth curving change in radius as a function of angle, but many other modulations such as triangular modulations of radius, sinusoidal modulations of radius, and many other modulation functions can be applied. It is also possible to create irregular shapes and even shapes that are not closed curves for shape discrimination testing.

Figure 5A:
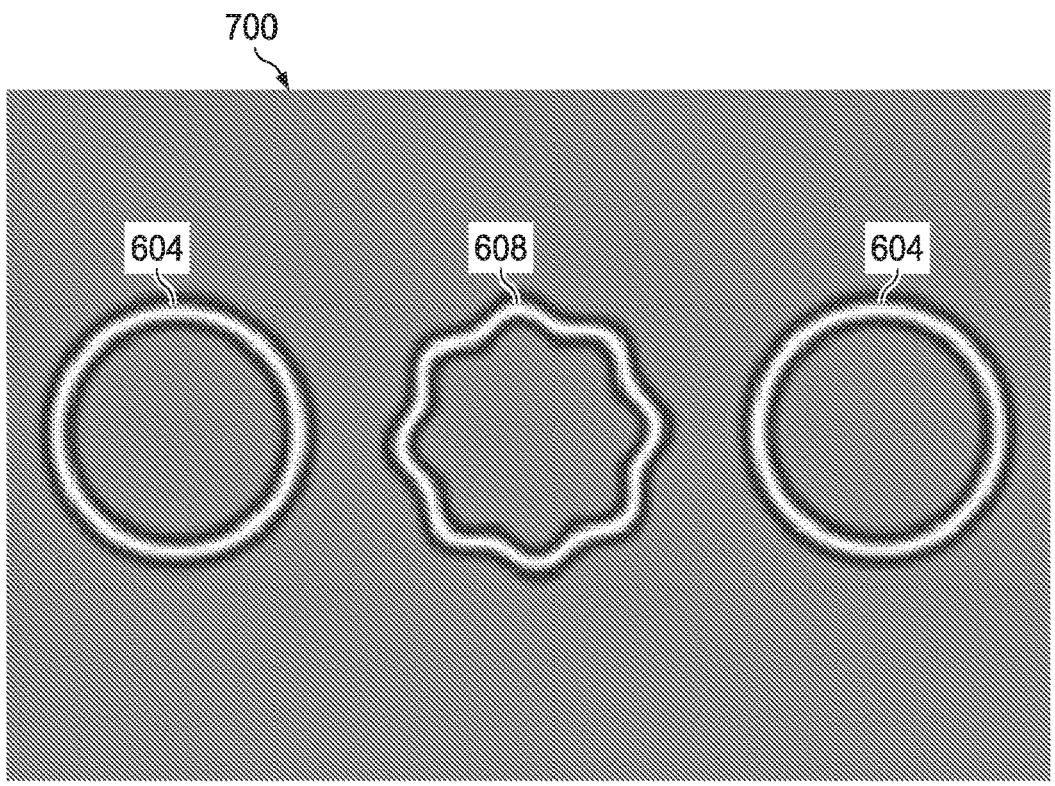
FIG. 5a shows a first three-way selection test with two circles and one modulated circle, all the shapes having pre-defined contrast as a function of radial dimension, and the modulated circle having strong modulation.
Figure 5B:
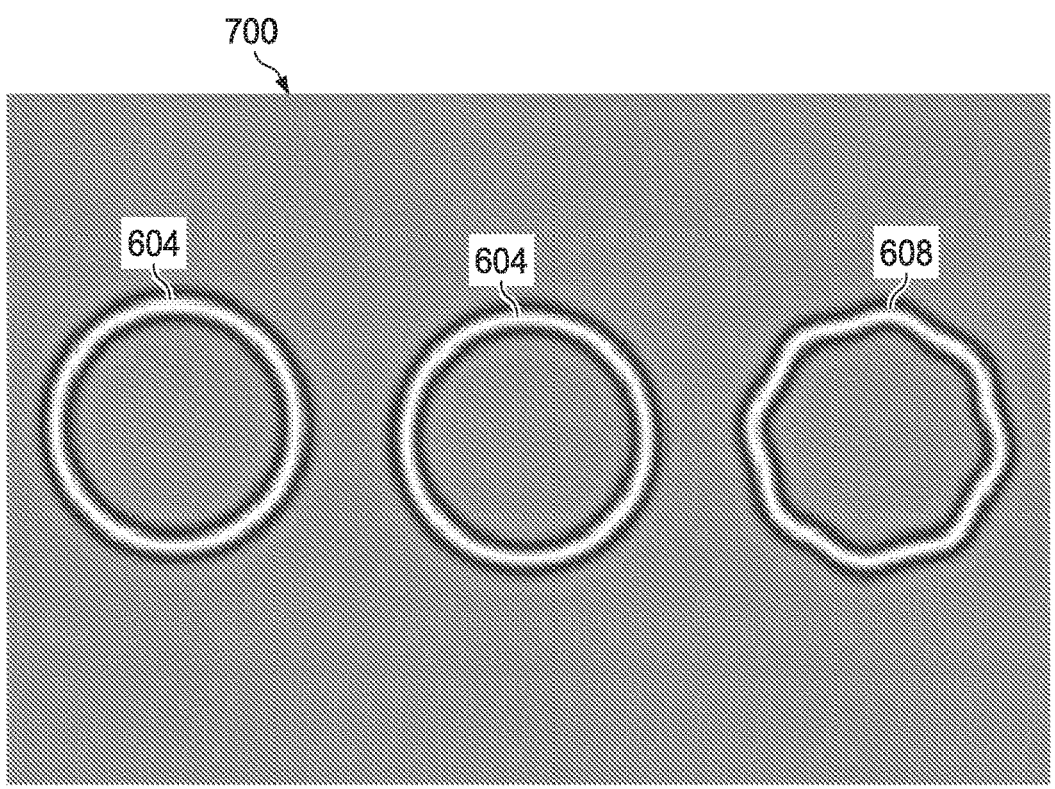
FIG. 5b shows a second three-way selection test with two circles and one modulated circle, all the shapes having pre-defined contrast as a function of radial dimension, and the modulated circle having moderate modulation.
Figure 5C:
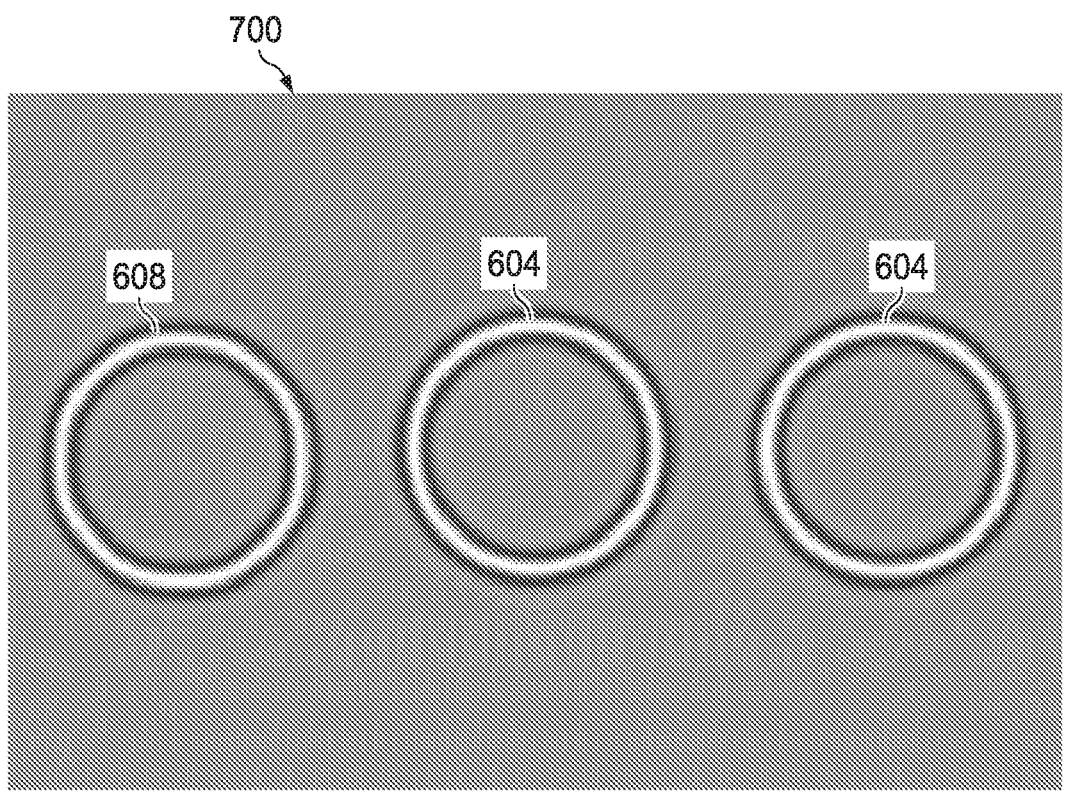
FIG. 5c shows a third three-way selection test with two circles and one modulated circle, all the shapes having pre-defined contrast as a function of radial dimension and the modulated circle having slight modulation.

In FIGS. 5a, 5b, and 5c a sequence of vision test images 700 that may be utilized on the handheld device 100 are shown. These would normally be shown to a user in turn and the next image would be shown once the user responds to the image being shown to them presently. The test images 700 are three-way selection shape discrimination tests. In the first test image 700 shown in FIG. 5a, two circles 604 and a modulated circle 608, all of which have pre-defined contrast as a function of radial dimension, are shown. Similar to the vision test described in FIGS. 3a and 3b, the three-way shape discrimination test image 700 is viewed by a user who selects which of the three or more shapes (in this embodiment three shapes are shown, but more can be used if desired) that is different from the others. This selection may be done by touching the display 104 over the shape being selected if a touch-screen or multi-touch display is used, or may be done with buttons, a mouse, cursor controls, audible inputs, gestures, or other techniques. In the embodiment shown, the different shape is clearly the modulated circle 608. In FIG. 5b, there are still two circles 604 and one modulated circle 608, but the modulation level of the modulated circle 608 has been reduced so that it is harder to distinguish from the circles 604. The order of the shapes has been changed so that the user must recognize that the modulated circle 608 is now to the right and no longer in the center location as it was in FIG. 5a and the relative location of all the shapes has been shifted slightly upwards, downwards and/or side-to-side to avoid causing the user to fixate at a specific point in the image. In addition, the modulation phase has been changed randomly to minimize the cues of localized deviation from circularity from one test trial to another. That is, the modulated circle 608 has also been rotated randomly so that the phase of the modulation may not provide any visual cues. As testing progresses, the user may then be shown the test image of FIG. 5c in which the modulated circle 608 is now to the far left and the modulation level is very small so that it is rather difficult to notice that it is different from the circles 604.

The vision testing approach shown in FIGS. 5a, 5b, and 5c offers several advantages. First, since it is desired that the user not fixate on a specific point in the images, there is no loss of accuracy if the user shifts their vision. In fact, it is desirable that the user make use of their broader vision. Second, the use of shapes such as the circle 604 and the modulated circle 608 that have contrast that varies with radial dimension makes the test less sensitive to small blurs in the display 104 that may be caused by manufacturing defects, dust, smudges, streaks, or other dirt and contamination. Also, since the shapes used in the images are intentionally blurred (by the radial variation of contrast), the test is less sensitive to imperfections of the visual accommodation of the user (that is, whether or not the user has good focusing ability and has a proper lens prescription if needed), and for substantially the same reasons, the test is also less sensitive to viewing distance from the user to the display 104. The embodiment shown in FIGS. 5a, 5b, and 5c used circles 604 and modulated circles 608, but other shapes (such as squares, triangles, irregular closed and open curves, etc.) that are somewhat blurred, have halos, have variable contrast, have shading, have lighter and darker pixels, or are otherwise made somewhat fuzzy may also provide good results as vision test images. And, of course, such shapes may be presented in a wide variety of colors, contrast levels, brightness levels and with other alterations to their construction and presentation.

Figure 6:
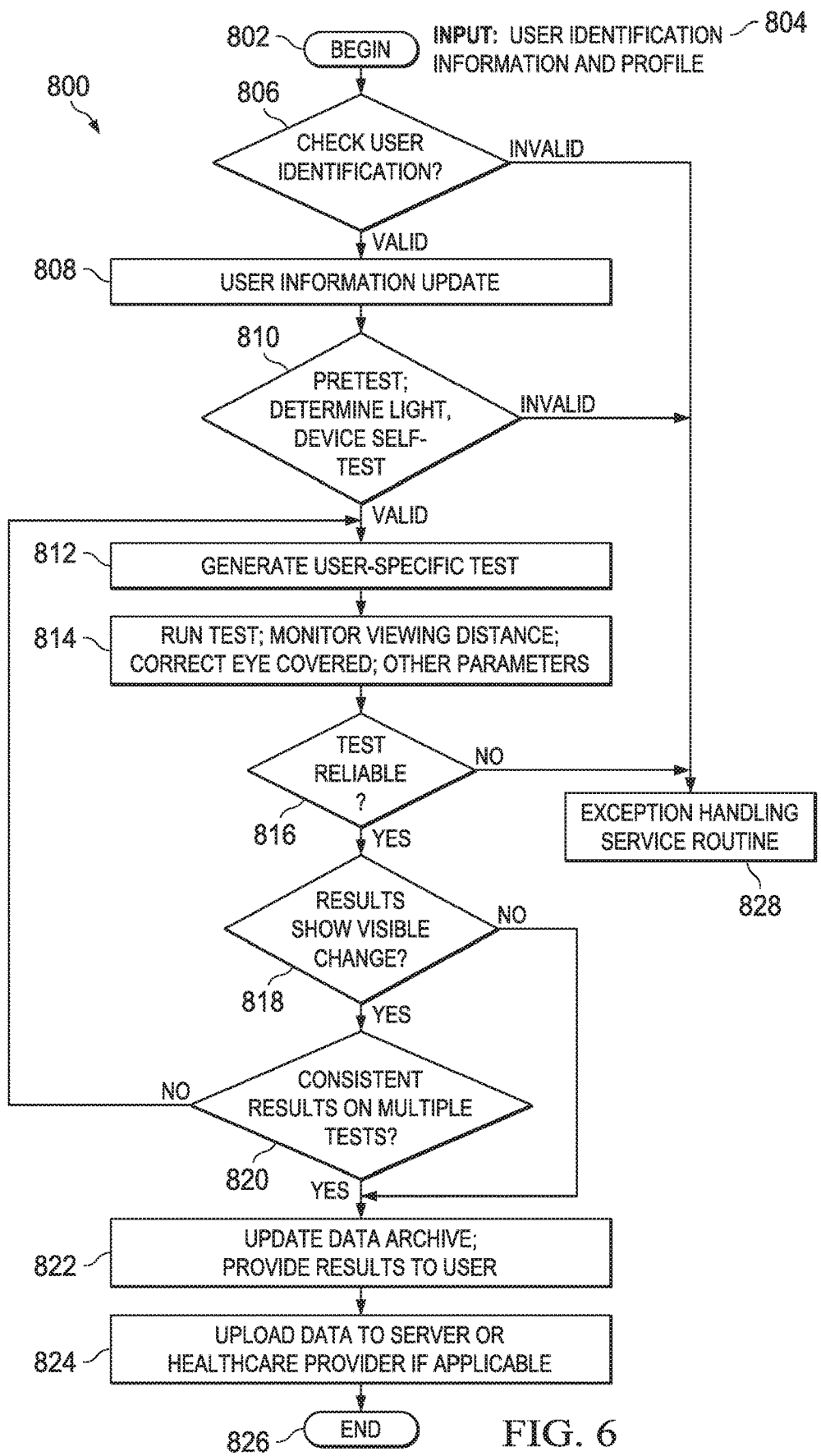
FIG. 6 shows a flow chart showing some elements of how a vision test routine may be controlled.

FIG. 6 shows a flow chart 800 showing some elements of how a vision test routine may be controlled through a computer program. While many program control flows are possible for the operation of the handheld device 100, several novel features of the flow chart 800 are included to help ensure accurate and reliable testing results. First step 802 indicates the beginning of the flow chart and the INPUT line 804 indicates that ID (identification) information for the user of the system and profile information about that person is made available to the program. This information may be received from prior inputs from the user, other programs, configuration information loaded by a health care provider or computer system administrator, over the internet, or via other means. First control step 806, may check the user's ID against the information received by the program from the INPUT line 804 and may verify the user's identity. The identity information used may include a photograph of the user, a password, electronic fingerprints, or other methods of verifying identification. Since the handheld device 100 may include a camera, fingerprint sensor, fundus camera, and means to collect other biometric data, there are potentially many ways to verify the user's identification. In addition to purposes for verifying the user's identification, this biometric data may be collected and stored in the handheld device to note the user's condition of health. Additionally, the biometric data may be date-stamped so that it can be associated to the user's health condition at a particular time and associated with particular vision testing results. Examples of biometric data include, without limitation, pupil dilation, iris color, eyelash growth, heart rate, blood pressure, ptosis, and results of other health condition measurements. Much of this biometric data can be assessed with the camera, but some may require to be collected through other auxiliary devices as well. In second step 808, user information may be updated once the user's identification has been verified. The user information may include information such as their preferred language, age, race, sex, blood pressure, glucose reading, resting heart rate, weight, medications, dosage levels, and other health related information. Biometric information, the results of health measurements and/or medical tests, the time and date of the dosage levels at which medications have been administered, side-effects the user may be experiencing from medications or treatments, and observations or comments the user may have regarding their state of health may be updated in second step 808 as well. Some of this information may come from an auxiliary device such as a glucometer, medication dosing aid, or other instruments and may be entered into the handheld device either manually by the user or automatically through an electronic interface. Medication dosing could also be recorded by the handheld device as a video to create a record of each medication dosing. The user information may also include other information about the user such as their email address, phone numbers, information regarding how to contact their health care provider, and other information the handheld device 100 may need to facilitate care for the user. It is noted that users may be likely to achieve the most accurate results when using their most comfortable language, hence, multilingual support based on the available user information may be important for the handheld device 100.

First control step 806 may also check to ensure that the software loaded on the handheld device 100 is a recent version and has not expired. The handheld device's 100 software may include expiration dates or a total number of times the software can be used before it is mandatory that the software be updated. This is an important safety feature as it ensures that old versions of the software cannot be used for a long time. Old software may have bugs that have been corrected in newer versions or newer software may have enhancements that make the vision testing more accurate, reliable, or beneficial in other ways. If the software version operating on the handheld device has expired or is not usable for some other reason, first control step 806 may pass control to exception handling service routine 828, where the user may be directed to download updated software, request customer service, or otherwise address the situation. It is noted that automatic software updates may also be provided and the handheld device 100 may simply access the internet according to a regular schedule and check for possible updates to be downloaded and installed. Alternatively, if specific handheld devices 100 are registered with a host computer system, updates may be sent to the specific handheld devices 100 as soon as they are ready for use.

Second control step 810 pretests, determines light levels, and self-tests handheld device 100. The pretest may be included to verify that the user is in a correct state to allow a valid vision test to be completed. This may be important to ensure that the user is alert, awake, not under the influence of medications, drugs, or alcohol, and is generally ready for the vision test. The pretest may be a short game, coordination check, or other check where the result is compared to past results for the user from prior testing. At this point in the program, the handheld device 100 may check the ambient light levels to ensure that the user is in an environment adequate for the vision testing. This may normally be done using the camera 112 to sense the ambient light levels, but may also be done with other light detectors such as a photodiode. Second control step 810 may also include a device self-test. In a self-test, the handheld device 100 may check its memory for proper functionality, and may check its interfaces and operating parameters for acceptable conditions. The self-test may direct the user to further test or calibrate the handheld device 100 if a problem is detected.

If second control step 810 has a valid outcome, a user-specific vision test or a standard test may be generated or accessed by the system software. The profile information from the INPUT line 804, the user information received in the second step 808, and possibly results from prior vision tests for the user may be used to determine what vision tests should be included. For example, a user with macular degeneration may benefit most from different tests than a patient with diabetic retinopathy. A user specific test generation is generated in third step 812 and once the user specific test is ready, fourth step 814 runs the test while monitoring the user's viewing distance, which eye the user has covered, and possibly other parameters. These other parameters might include monitoring an accelerometer or other motion sensor to sense if the user is shaking or otherwise moving more than would be acceptable for an accurate test result. It may also include monitoring of the ambient light levels, and/or checking for the presence of glare. The time the user takes for each test input may also be monitored so that interruptions of the testing or very long response times may be noted as possible indications of an invalid test. If any situations arise during the vision test that may compromise the accuracy of the results, the user may be notified to correct them. And if a correction is not made, the results may be marked to indicate they were received under questionable operating circumstances.

Some means to allow the user to pause or abort testing may be included in fourth step 814 functions, and also, may be included in other areas of the flow chart 800 as well. This is beneficial as the user may be interrupted with a phone call, visitor, or have some other reason to want to stop testing immediately and resume later. The ability to pause and resume testing may be limited to short interruptions as the reliability of the test may be compromised if the user's condition, ambient conditions, or other factors have changed since testing was paused. Consequently, a time out function may be necessary if a pause feature is included. It is noted that records of partial tests, aborted tests, and paused tests (whether or not they timed out) may be stored in the handheld device 100, but should be properly recorded to ensure that they are not confused with valid and complete test results.

Third control step 816 checks to ensure that results from the test run in step 814 are reliable. This includes checking to ensure that all the parameters being monitored during the course of the test, such as viewing distance and proper eye coverage, etc., are nominal. And it may also include analysis of the test results to ensure consistency. That is, the vision test may be designed to include some redundancy in testing so that user responses on various tests are consistent with each other and indicate that the user took the test properly and was not guessing, making random inputs, or otherwise taking the test capriciously. One way this may be achieved is to occasionally present the user with a "freebie" test. That is, while the normal course of a vision test may be to subsequently make it more difficult for the user to distinguish the features of the test image (this was illustrated in the explanation of FIGS. 5a, 5b, and 5c), it may be beneficial to occasionally give the user a rather easy test image to respond to. This is referred to as a "freebie". If the user doesn't quickly and accurately respond to the "freebie" it may be a sign that the user is not taking the test actively, is tired, or is somehow otherwise impaired. Additionally, occasionally offering the user a "freebie" test image may help the user maintain confidence and keep trying to master the test.

Third control step 816 may also check specifically for false negative test results. False negative results are especially troublesome as they may indicate to the user that their condition is okay, when they may actually have a vision condition that needs attention. A false negative may be the result of the user cheating on the test by moving the handheld device 100 closer to them than they should for some test decisions, studying the test image for a long time, asking a person with them what answer to provide, and possibly other ways. Additionally, a false negative may occur if the test is not specifically sensitive to the user's condition or possibly for other reasons. For this reason, it may be important to ensure that all operating parameters (user condition, ambient light conditions, response timing, etc.) are consistent with accurate testing before a negative test result is provided.

If the results appear to be reliable, third control step 816 passes control to fourth control step 818 which may determine whether the test results show a significant change in vision. As noted previously, a substantial benefit of vision monitoring may be gained in noting if changes in a user's vision have occurred from previous testing. Hence, fourth control step 818 may check specifically for this and direct the program to fifth control step 820 which checks if an additional test is needed if significant changes may have occurred. If fifth control step 820 finds that prior test results are not consistent (or if there are no prior results to compare to), a new user-specific test may be generated by third step 812 so that the user is not influenced by remembering how he or she responded to the prior test. That is, while the additional test may substantially test for the same conditions as the prior test, it may be presented so that the results are not influenced by the user's perceptions from the prior test. Fourth control step 818 and fifth control step 820 may also make other assessments. For example, if this is the first time a new user is receiving the test, it may direct control to complete multiple tests simply to verify consistency of the test readings and to more rapidly build a database of results for the user.

If acceptable results are found so that no additional tests are needed, fourth control step 818 passes control to fifth step 822 where a data archive kept in the handheld device 100 may be updated with the new results and results may be provided to the user. Once again, if fourth control step 818 indicates a change in the users test results, control passes to fifth control step 820 where the results of the previous test, if one has already been completed, are compared to the results of the present test. If a sufficient number of tests (the system could be configured for any number of additional tests as desired) show consistent results, control also passes on to fifth step 822 for data archiving and presentation of the results to the user.

Fifth step 822 may perform two very important functions. First, it updates the data archives kept in the handheld device 100. The archives may include all information about the testing that was just completed. For example, the date and time the test was taken, identification of the handheld device 100 used, where the test was taken (if position information is available), how the user's identification was validated, a picture of the user, the room conditions, the distance from the user to the handheld when the test was taken, the time taken for and the result of each response the user gave in the course of the test, the length of any pauses in the testing, any invalid results, any special conditions that arose, the results of all tests given, and other information may be archived. Additional information such as screen shots of the handheld device's 100 display 104 at various points of the testing, and especially the screen shot presented to the user providing the results of their test, may also be archived. Of course, additional parameters may be archived, or for some embodiments, it may not be necessary to include all the information listed here. In any case, however, sufficient information may be archived so that a substantially complete and accurate record of the testing is kept.

The second key function of fifth step 822 may be to notify the user of the results of his or her test. This may be done visually on the handheld device 100 display 104, audibly, or by other means. But in any case, the results provided to the user may include their specific test scores and also some information about what the scores mean. That is, the handheld device 100 may assure the user that their scores are within reasonable bounds of their past scores. Or, if the user's vision has changed such that the handheld device 100 concludes that a professional evaluation is warranted, the handheld device 100 may direct the user to contact their health care provider for an evaluation. Of course, the handheld device 100 may also be used to keep track of the user's appointments including their scheduled visits with healthcare providers. So in some cases, the handheld device 100 may produce normal results for vision testing, but still remind the user that they have a regular appointment with a healthcare professional.

Additionally, it may be beneficial to pass inspirational or encouraging messages to the user. As it has been scientifically demonstrated that a positive outlook leads to better physical health, the user may benefit if they are given positive encouragement in the course of their testing and especially when their results are provided to them. Other information that may be beneficial to the user such as recommendations for a healthy diet with exercise, advertising and branding information, or other information may also be passed to the user from the handheld device 100 at multiple points through the course of its use and, in particular, when the user is provided and/or is about to be provided their testing results. Of course, the inspirational and other messages may be tailored to the user's specific preferences through information stored in the handheld device 100. For example, if it is known to the handheld device 100 that the user is trying lose weight, some encouragement consistent with this goal may be especially beneficial. Similarly, if the user's religion is known, inspirational messages can be tailored to be appealing to them more specifically.

Control then passes from fifth step 822 to sixth step 824 where the testing results may be uploaded to a healthcare provider, clinical study coordinator, or other appropriate entity. The testing results may also be uploaded to a data server. Users with especially acute conditions, for example, may want a professional to review their testing results on an ongoing basis. Or, since the handheld device 100, could be damaged, destroyed, lost, or stolen, the user may want their results to be stored on a computer system server so that they can be recovered if needed. In either case, wired or wireless networking technology such as DSL, fiber optics, wireless LAN, wireless WAN, or other wired or wireless data transmission technologies may be used to upload the data. Some user's may want email messages with their test results sent to specific email addresses and than can also be completed in sixth step 824 if desired.

It is also possible for data uploaded from the handheld device 100 to be used in the construction of databases of information that may be used to enhance knowledge of various testing and treatment routines. That is, if a user is known to be taking certain medication, uploading and analyzing their vision testing results allows comparison of their results with others so that a substantially complete and accurate knowledge of the effectiveness of certain treatments may be assessed. This information may be beneficial to developers of treatments and especially in the conduction of medical trials to assess the efficacy of treatments. In addition to the scientific benefits of such data collection, business models in which companies or individuals wanting access to certain data may financially compensate a handheld device 100 user, or a provider of vision testing technology, may also be possible. As an example, a health insurance provider may incentivize users to take regular tests and possibly also upload their test results in the interests of making overall disease management and/or treatment more cost effective.

In the course of the program running the vision testing on the handheld device 100 as shown in the flow chart 800 in FIG. 6, several control steps pass control to exception handling service routine 828. First control step 806, second control step 810, and third control step 816 all include conditions for which negative or invalid results result in sending control to exception handling service routine 828. Depending on the nature of the invalid or negative result, and depending on electronic diagnostics and self-testing the handheld device 100 performs on itself to ensure proper operation, exception handling service routine 828 may direct the user to perform different functions so that proper testing can resume or be initiated. For example, if the user's identification fails, exception handling service routine 828 may simply notify the user and allow them to try again. However, if the self-test of the handheld device 100 has failed, the user may be directed to test, service, or calibrate the handheld device 100. Other conditions may be dealt with in appropriate manners as well. If the room ambient light is too bright, the user may be directed to change it. If inconsistent test results were determined and the test was deemed unreliable, the user may be notified and asked to take the test another time. If repeated unreliable results occur, the user may be directed to seek a professional evaluation from their healthcare provider. Since the handheld device 100 may make very many measurements and use very many techniques to ensure an accurate and reliable test, it is not practical to list many dozens or even hundreds of them here. However, the overall flow of the flow chart 800 makes it clear that the handheld device 100 will use many techniques to ensure accurate and dependable results.

Once all testing, archiving, user notifications and other functions are completed, program control passes to seventh step 826 where operation is ended and the program ceases operation until it is restarted. In some cases, the handheld device 100 may include alarm functions to alert a user that they have a scheduled vision test to complete. In such a case, the handheld device 100 may start up automatically and send audible and/or visible or other signals to the user to remind them to take their test. The handheld device 100 may also include other calendar, appointment management, or other user convenience software. Additionally, it may be synchronized or updated by other calendar management software so that the user may conveniently keep track of their personal appointments along with their testing schedule, heath care provider appointments, medication schedule, reminders to take vitamins and/or exercise, and other aspects of their overall care.

Figure 7A:
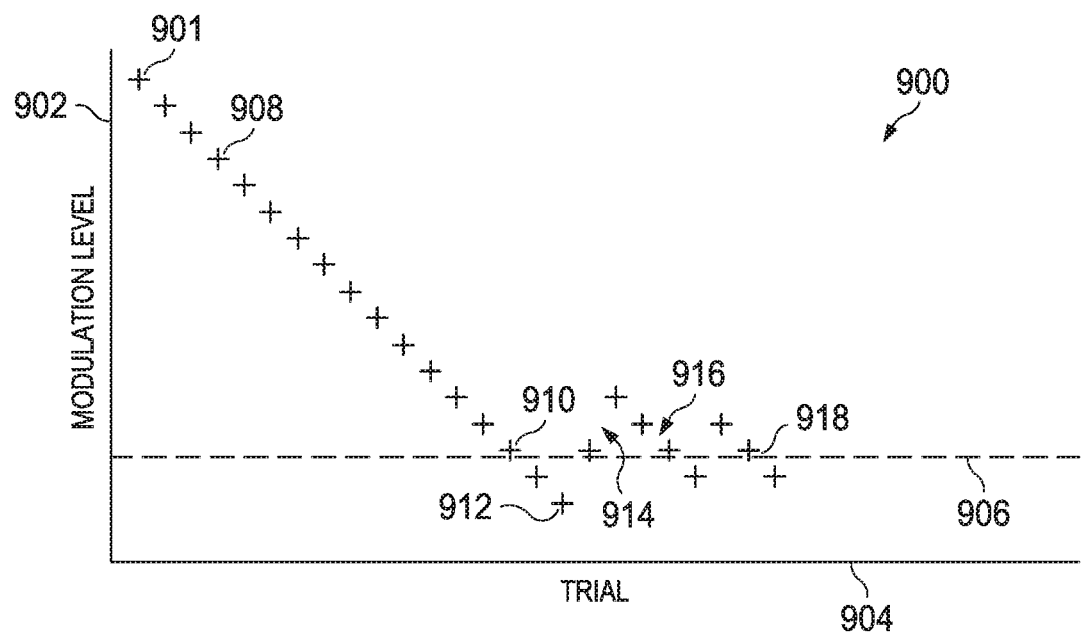
FIG. 7a shows a graphical result of a shape discrimination vision test.
Figure 7B:
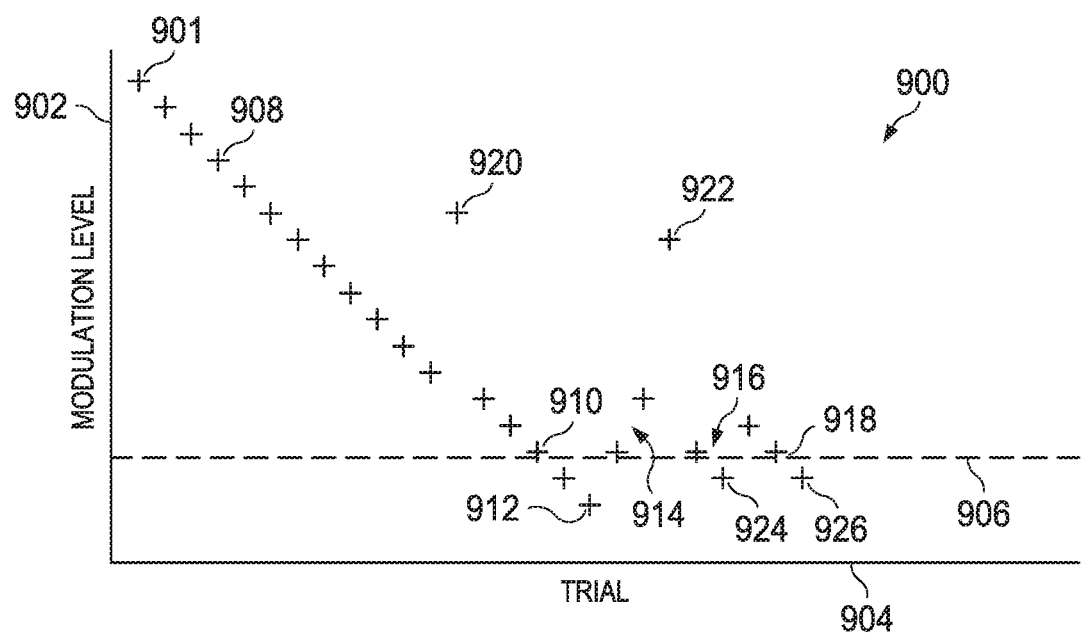
FIG. 7b shows a graphical result of a shape discrimination vision test that includes freebies.

FIG. 7a shows a graphical result of a shape discrimination vision test 900. The first trial image is represented by the first cross 901 which is shown at an elevated modulation level as it is positioned at a high level on the vertical axis 902. Note that the vertical axis 902 represents modulation level and this is clear in FIG. 7a as the words "Modulation Level" are shown as a title on the vertical axis 902. Modulation level as shown in FIGS. 7a and 7b refers to the amplitude of the modulation of a modulated shape such as the modulated circle 608 of FIG. 4b, or FIGS. 5a, 5b, and 5c. Subsequent trials are represented in FIG. 7a as progressing to the right along the horizontal axis 904 that is also labeled with the word "Trial". Each subsequent trial is also represented by a cross 908 and the modulation level for the next several trials are shown as decreasing with each subsequent trial. This approach is beneficial as a very large modulation level may be used for the first few trials so that the user intuitively learns that the modulation will decrease on subsequent trials if correct answers are provided. Of course, as explained with regard to FIGS. 5a, 5b, and 5c, as the modulation level is decreased, it will eventually become difficult to accurately determine a modulated shape versus an un-modulated shape (i.e. a shape with no modulation) so the user will invariably make a mistake at some point. The mistake trial 912 illustrates this and shows that if a mistake is made, the modulation increases on a subsequent trial. Once correct responses to a trial resume, the modulation will again decrease on subsequent trials. It is noted that an amount modulation increases 914 when a mistake is made may be different from an amount modulation is decreased 916 when a correct answer is entered. After some number of trials, an accurate representation of the limit of the user's modulation threshold 906 may be estimated. The modulation threshold 906 may be determined from the data in a number of ways. One approach would be to take the modulation threshold 906 to be the level at which an equal number of decreasing and increasing modulation trials (i.e., an equal number of mistakes and correct result entries) are made over some number of past trials. For example, the modulation threshold 906 could be taken as the level at which an equal number of correct results and mistakes occurred over the last four trials. The modulation threshold 906 might also be taken as the modulation level that was crossed with correct (or incorrect) answers some fixed number of times. For example, in FIG. 7a, the modulation threshold 906 is a level that was crossed three times with correct answers. The third correct crossing 918 in FIG. 7a illustrates this. Or the modulation threshold might also be taken as the mean of several reversals (the level changes from correct to incorrect or from incorrect to correct). Another way to determine the threshold might be to fit a mathematical function that describes the threshold behavior of the visual system to the percent correct rates at various testing levels. The reliability of the threshold estimation may be assessed by analyzing fitting parameters and by comparing threshold values obtained with various threshold determination methods.

FIG. 7b shows a similar graphical result of a shape discrimination vision test 900 to that shown in FIG. 7a, but freebie 920 and freebie 922 are included. As previously described, a freebie trial is a trial in which the user is presented with a rather large modulation with the expectation that it should be an easy test for them to answer correctly. Hence, observation of the user's replies to a freebie is one way of ensuring that the user is actively engaged in the test and isn't just guessing. Another measure of the user's ability to correctly take the test is the consistency of the level at which mistakes occur as the test trials progress. In FIG. 7b, the first mistake trial 912, the second mistake trial 924 and the third mistake trial 926 all occur at similar modulation levels. Consequently, the confidence in the modulation threshold 906 level for the user is relatively high as the user appears to be consistent in the level of modulation reached before a mistake is made. Other ways of assessing the user's consistency include consistently correct answers for higher modulation levels above the modulation threshold 906, and other possible statistical or other mathematical analysis techniques. It is noted that the amount the modulation is varied after the occurrence of a freebie may resume from the level of modulation prior to the freebie, may decrease from the level of modulation prior to the freebie assuming the freebie trial was answered correctly, or may follow other rules for variation of modulation including random variation of modulation rules and other rules.

Figure 8A:
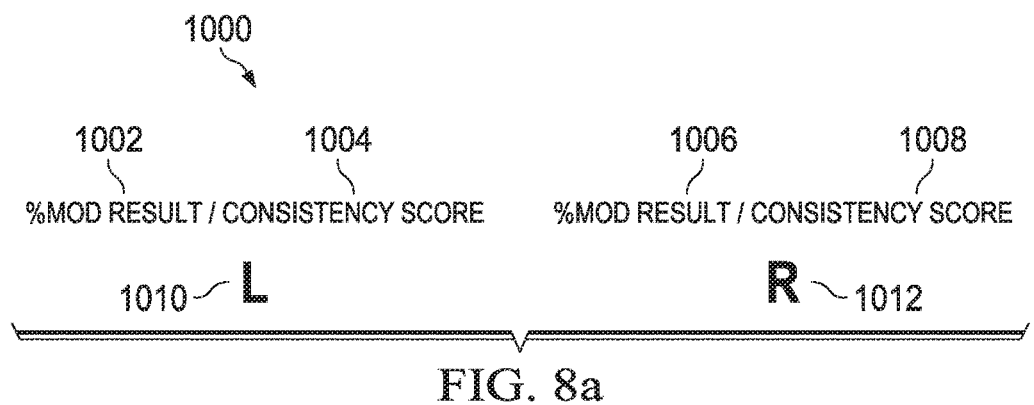
FIG. 8a shows a quantitative result presentation for a shape discrimination vision test.

FIG. 8a illustrates a quantitative result presentation 1000 for providing results to the user and/or tabulating results of a shape discrimination test. The L 1010 indicates that the results above it are for the left eye and the R 1012 indicates that the results above it are for the right eye. The % Mod Result for the left eye 1002 is the modulation threshold 906 shown in FIGS. 7a and 7b for the left eye of the user and the % Mod Result for the right eye 1006 is the modulation threshold 906 for the right eye of the user. The % Mod Result for the left eye 1002 and the % Mod Result for the right eye 1006 may be presented as simple percentages of modulation, proportions of modulation to circle radius (or another key dimension whatever shape is used), in the well-known MAR (Minimum Angle of Resolution) measure, or in logMAR (the logarithm of MAR), or in other quantitative or relative measurement formats. The left eye consistency score 1004 and the right eye consistency score 1008 are consistency measures as previously discussed for the users left eye and right eye tests respectively. Providing a consistency score of some sort to the user coaches them on their test taking ability and reinforces the need to take the vision test carefully and actively. The left eye consistency score 1004 and the right eye consistency score 1008 are much like video game scores in that they tell the user how well they took the test. Storing the left eye consistency score 1004 and the right eye consistency score 1008 in the handheld device's 100 memory and making it a part of the test archive for the user is useful as it provides an indication of how well the test was taken, and hence, to what level the result may be trusted.

Figure 8B:
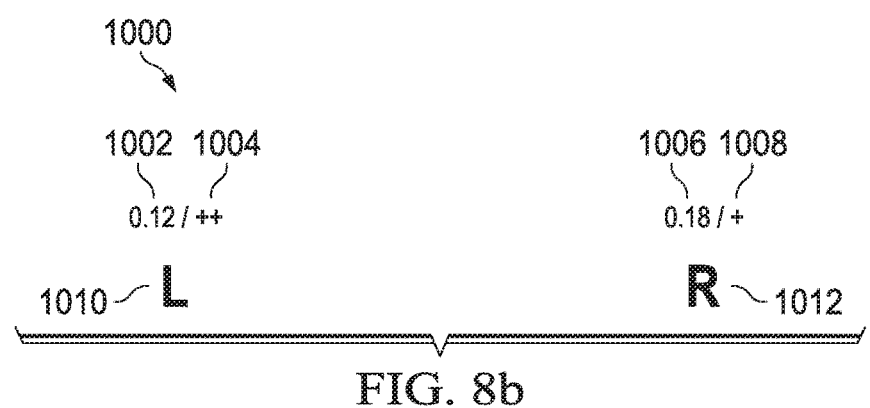
FIG. 8b shows a numerical example of a quantitative result presentation for a shape discrimination vision test.

In FIG. 8b, an example quantitative result presentation 1000 is provided with numerical example results for the % Mod Result for the left eye 1002 and the left eye consistency score 1004 shown above the L 1010; and with % Mod Result for the right eye 1006 and a right eye consistency score 1008 shown above the R 1012. Note that the left eye consistency score 1004 and the right eye consistency score 1008 as presented in FIG. 8b are not numerical, but are represented as ++ and +, respectively, indicating relatively how consistent the user was in taking the tests. Numerical scores are also possible, but relative scores using stars, smiling or frowning faces, different colors, or other approaches may be beneficial in providing a general indication of how consistently the user took the test. Additionally, the % Mod Result for the left eye 1002 and the % Mod Result for the right eye 1006 may also be provided as relative scores if desired. Relative scores such as good/moderate/poor, normal/borderline/abnormal, and many other relative scores are possible.

Figure 8C:
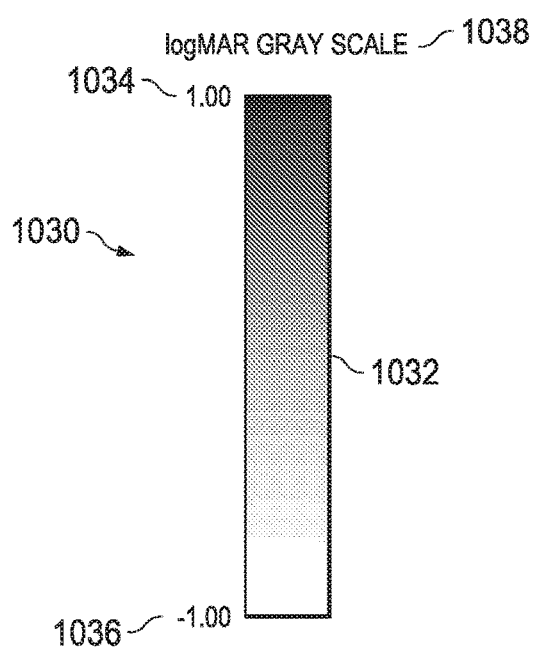
FIG. 8c shows a logMAR gray scale result presentation.

FIG. 8c shows another example technique for result presentation. A logMAR gray scale 1030 is shown including a title 1038, a lower gray scale limit 1036, an upper gray scale limit 1034, and a gray scale 1032. In FIG. 8c, the title 1038 identifies the result presentation of the logMAR gray scale 1030 as "logMAR Gray Scale", the lower gray scale limit 1036 is illustrated as "−1.00" and the upper gray scale limit 1034 is illustrated as "1.00". The gray scale 1032 shows a range from white for results near the lower gray scale limit 1036 to black for results near the upper gray scale limit 1034. For example, a test score may be represented by using a gray level between the upper gray scale limit 1034 and the lower gray scale limit 1036. The accuracy of the test score may be represented by the extension of that gray level, or a band of gray levels centered at the one that represents the test score. The narrower the gray level band, the more accurate or consistent the test score. A wide range of other options for using a segment of gray region within a gray scale 1032 include showing a result presentation in which the center of a gray region represents a test score and the size, shape or other aspects of the gray region represent the consistency of the user in taking the test. Of course, many variants including use of variable color shades instead of a gray scale 1032, varying shapes, sizes, and other variations may be used.

Although the description above contains many specificities, these should not be construed as limiting the scope of the invention, but as merely providing illustrations of some of the presently preferred embodiments of this invention. Thus the scope of the present invention should be determined by the appended claims and their legal equivalents, rather than by the examples given. Those skilled in the art to which this application relates will appreciate that other and further additions, deletions, substitutions and modifications may be made to the described embodiments.

What is claimed is:

1. A method to self-test vision of a user for use with a handheld vision tester, comprising:
receiving image data of the user's face;
determining dimensions of features of the user's face based on said received image data;
computing, using the handheld vision tester, a user viewing distance based on said determined dimensions, where the user viewing distance represents a distance between the user and the handheld vision tester;
in response to computing the user viewing distance, displaying a vision test;
receiving user input responses to the vision test; and
outputting results of the vision test from said user input responses.

2. The method of claim 1, wherein said determining dimensions comprises measuring at least one of: a distance between pupils of eyes of said user, a distance between outer eye sockets of said user, a distance between said pupils and a bottom of a nose of said user, or a combination thereof.

3. The method of claim 1, wherein said displayed vision test comprises a test image with an aspect adjusted based on said computed user viewing distance.

4. The method of claim 3, wherein said adjusted aspect comprises a size of said test image.

5. The method of claim 3, wherein said adjusted aspect comprises a sharpness of said test image.

6. The method of claim 1, further comprising computing vision test results based on said computed user viewing distance.

7. The method of claim 1, further comprising storing said computed user viewing distance in said handheld vision tester.

8. A handheld vision tester for vision self-testing by a user, comprising:
- a camera configured to receive image data of the user's face;
- a display configured to present a vision test to said user; and
- a control configured to allow said user to input responses to the vision test,
  - wherein said handheld vision tester is configured to:
    - determine dimensions of features of the user's face based on said received image data;
    - compute a user viewing distance based on said determined dimensions, where the user viewing distance represents a distance between the user and the handheld vision tester;
    - in response to computing the user viewing distance, display the vision test; and
    - output results of the vision test from said user input responses.

9. The handheld vision tester of claim 8, wherein said dimensions includes at least one of: a distance between pupils of eyes of said user, a distance between outer eye sockets of said user, a distance between said pupils and a bottom of a nose of said user, or a combination thereof.

10. The handheld vision tester of claim 8, wherein said determined vision test comprises a test image with an aspect adjusted based on said computed user viewing distance.

11. The handheld vision tester of claim 10, wherein said adjusted aspect comprises a size of said test image.

12. The handheld vision tester of claim 10, wherein said adjusted aspect comprises a sharpness of said test image.

13. The handheld vision tester of claim 8, further wherein said handheld vision tester is configured to compute vision test results based on said computed user viewing di stance.

14. One or more computer-readable non-transitory storage media embodying software that is operable when executed to:
- receive image data of the user's face;
- determine dimensions of features of the user's face based on said received image data;
- compute a user viewing distance based on said determined dimensions, where the user viewing distance represents a distance between the user and the handheld vision tester;
- in response to computing the user viewing distance, display a vision test;
- receive user input responses to the vision test; and
- output results of the vision test from said user input responses.

15. The computer-readable non-transitory storage media of claim 14, wherein said determine dimensions comprises measuring at least one of: a distance between pupils of eyes of said user, a distance between outer eye sockets of said user, a distance between said pupils and a bottom of a nose of said user, or a combination thereof.

16. The computer-readable non-transitory storage media of claim 14, wherein said displayed vision test comprises a test image with an aspect adjusted based on said computed user viewing distance.

17. The computer-readable non-transitory storage media of claim 16, wherein said adjusted aspect comprises a size of said test image.

18. The computer-readable non-transitory storage media of claim 16, wherein said adjusted aspect comprises a sharpness of said test image.

19. The computer-readable non-transitory storage media of claim 14, further comprising compute vision test results based on said computed user viewing distance.

20. The computer-readable non-transitory storage media of claim 14, further comprising store said computed user viewing distance in said handheld vision tester.

\* \* \* \* \*